(12) United States Patent
Will et al.

(10) Patent No.: US 7,892,274 B2
(45) Date of Patent: Feb. 22, 2011

(54) APPARATUS AND METHODS FOR DEPLOYMENT OF VASCULAR PROSTHESES

(75) Inventors: Allan Will, Atherton, CA (US); Bernard Andreas, Redwood City, CA (US); Sunmi Chew, San Jose, CA (US)

(73) Assignee: Xtent, Inc., Menlo Park, CA (US)

( * ) Notice: Subject to any disclaimer, the term of this patent is extended or adjusted under 35 U.S.C. 154(b) by 1028 days.

(21) Appl. No.: 11/560,739

(22) Filed: Nov. 16, 2006

(65) Prior Publication Data
US 2007/0129733 A1 Jun. 7, 2007

Related U.S. Application Data

(63) Continuation of application No. 10/637,713, filed on Aug. 8, 2003, now Pat. No. 7,309,350, which is a continuation-in-part of application No. 10/412,714, filed on Apr. 10, 2003, now Pat. No. 7,137,993, which is a continuation-in-part of application No. 10/306,813, filed on Nov. 27, 2002, now abandoned.

(60) Provisional application No. 60/364,389, filed on Mar. 13, 2002, provisional application No. 60/336,967, filed on Dec. 3, 2001.

(51) Int. Cl.
*A61F 2/06* (2006.01)

(52) U.S. Cl. .................................... 623/1.11
(58) Field of Classification Search ................ 606/108, 606/191–198; 623/1.11–1.12, 1.16
See application file for complete search history.

(56) References Cited

U.S. PATENT DOCUMENTS

| 4,069,825 A | 1/1978 | Akiyama |
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |

(Continued)

FOREIGN PATENT DOCUMENTS

DE 195 31 659 3/1997

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner*—Kevin T Truong
(74) *Attorney, Agent, or Firm*—Kilpatrick Townsend & Stockton LLP

(57) ABSTRACT

Apparatus for delivering stents to body lumens include one or more tubular prostheses carried at the distal end of a catheter shaft, a sheath slidably disposed over the prostheses, and a guidewire tube extending from within the sheath to the exterior of the sheath through an exit port in a sidewall thereof. A guidewire extends slidably through the guidewire tube. The sheath can be moved relative to the catheter shaft and the guidewire tube to expose the prostheses for deployment. Methods of delivering stents are also provided.

40 Claims, 10 Drawing Sheets

U.S. PATENT DOCUMENTS

| | | |
|---|---|---|
| 4,733,665 A | 3/1988 | Palmaz |
| 4,739,762 A | 4/1988 | Palmaz |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,391,172 A | 2/1995 | Williams et al. |
| 5,421,955 A | 6/1995 | Lau et al. |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,531,735 A | 7/1996 | Thompson |
| 5,534,007 A | 7/1996 | St. Germain et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,593,412 A | 1/1997 | Martinez et al. |
| 5,607,444 A | 3/1997 | Lam |
| 5,607,463 A | 3/1997 | Schwartz et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanski Stockert et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,697,948 A | 12/1997 | Marin et al. |
| 5,697,971 A | 12/1997 | Fischell et al. |
| 5,702,418 A | 12/1997 | Ravenscroft |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A * | 11/1998 | Poncet ................. 623/1.11 |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A * | 11/1999 | Mertens et al. ......... 604/164.13 |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,997,563 A | 12/1999 | Kretzers et al. |
| 6,004,328 A | 12/1999 | Solar |
| 6,007,517 A | 12/1999 | Anderson |
| 6,022,359 A | 2/2000 | Frantzen |
| 6,022,374 A | 2/2000 | Imran |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,056,722 A | 5/2000 | Jayaraman |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,143,016 A | 11/2000 | Bleam et al. |
| 6,165,167 A | 12/2000 | Delaloye |
| 6,165,210 A | 12/2000 | Lau et al. |
| 6,179,878 B1 | 1/2001 | Duering |
| 6,183,509 B1 | 2/2001 | Dibie |
| 6,187,034 B1 | 2/2001 | Frantzen |

| | | | | | | |
|---|---|---|---|---|---|---|
| 6,190,402 B1 | 2/2001 | Horton et al. | 6,676,695 B2 | 1/2004 | Solem | |
| 6,196,995 B1 | 3/2001 | Fagan | 6,679,909 B1 | 1/2004 | McIntosh et al. | |
| 6,200,337 B1 | 3/2001 | Moriuchi et al. | 6,685,730 B2 | 2/2004 | West et al. | |
| 6,238,991 B1 | 5/2001 | Suzuki | 6,692,465 B2 | 2/2004 | Kramer | |
| 6,241,691 B1 | 6/2001 | Ferrera et al. | 6,699,280 B2 | 3/2004 | Camrud et al. | |
| 6,251,132 B1 | 6/2001 | Ravenscroft et al. | 6,699,724 B1 | 3/2004 | West et al. | |
| 6,251,134 B1 | 6/2001 | Alt et al. | 6,702,843 B1 | 3/2004 | Brown | |
| 6,254,612 B1 | 7/2001 | Hieshima | 6,709,379 B1 | 3/2004 | Brandau et al. | |
| 6,254,628 B1 | 7/2001 | Wallace et al. | 6,709,440 B2 | 3/2004 | Callol et al. | |
| 6,258,117 B1 | 7/2001 | Camrud et al. | 6,712,827 B2 | 3/2004 | Ellis et al. | |
| 6,264,688 B1 | 7/2001 | Herklotz et al. | 6,712,845 B2 | 3/2004 | Hossainy | |
| 6,267,783 B1 | 7/2001 | Letendre et al. | 6,723,071 B2 | 4/2004 | Gerdts et al. | |
| 6,273,895 B1 | 8/2001 | Pinchuk et al. | 6,736,842 B2 | 5/2004 | Healy et al. | |
| 6,273,911 B1 | 8/2001 | Cox et al. | 6,743,219 B1 * | 6/2004 | Dwyer et al. | 623/1.11 |
| 6,273,913 B1 | 8/2001 | Wright et al. | 6,743,251 B1 | 6/2004 | Eder | |
| 6,312,458 B1 | 11/2001 | Golds | 6,761,734 B2 | 7/2004 | Suhr | |
| 6,315,794 B1 | 11/2001 | Richter | 6,778,316 B2 | 8/2004 | Halas et al. | |
| 6,319,277 B1 | 11/2001 | Rudnick et al. | 6,800,065 B2 | 10/2004 | Duane et al. | |
| 6,322,586 B1 | 11/2001 | Monroe et al. | 6,825,203 B2 | 11/2004 | Pasternak et al. | |
| 6,325,823 B1 | 12/2001 | Horzewski et al. | 6,837,901 B2 | 1/2005 | Rabkin et al. | |
| 6,334,871 B1 | 1/2002 | Dor et al. | 6,849,084 B2 | 2/2005 | Rabkin et al. | |
| 6,340,366 B2 | 1/2002 | Wijay | 6,852,252 B2 | 2/2005 | Halas et al. | |
| 6,344,272 B1 | 2/2002 | Oldenburg et al. | 6,855,125 B2 | 2/2005 | Shanley | |
| 6,357,104 B1 | 3/2002 | Myers | 6,858,034 B1 | 2/2005 | Hijlkema et al. | |
| 6,375,676 B1 | 4/2002 | Cox | 6,878,161 B2 | 4/2005 | Lenker | |
| 6,379,365 B1 | 4/2002 | Diaz | 6,884,257 B1 * | 4/2005 | Cox | 623/1.11 |
| 6,383,171 B1 | 5/2002 | Gifford et al. | 6,893,417 B2 | 5/2005 | Gribbons et al. | |
| 6,409,753 B1 | 6/2002 | Brown et al. | 6,896,695 B2 | 5/2005 | Mueller et al. | |
| 6,415,696 B1 | 7/2002 | Erickeson et al. | 6,918,928 B2 | 7/2005 | Wolinsky et al. | |
| 6,419,693 B1 | 7/2002 | Fariabi | 6,939,376 B2 | 9/2005 | Shulz et al. | |
| 6,425,898 B1 | 7/2002 | Wilson et al. | 6,945,989 B1 | 9/2005 | Betelia et al. | |
| 6,428,811 B1 | 8/2002 | West et al. | 6,945,995 B2 | 9/2005 | Nicholas | |
| 6,451,025 B1 | 9/2002 | Jervis | 6,951,053 B2 | 10/2005 | Padilla et al. | |
| 6,451,050 B1 | 9/2002 | Rudakov et al. | 6,964,676 B1 | 11/2005 | Gerberding et al. | |
| 6,464,720 B2 | 10/2002 | Boatman et al. | 7,005,454 B2 | 2/2006 | Brocchini et al. | |
| 6,468,298 B1 | 10/2002 | Pelton | 7,037,327 B2 | 5/2006 | Salmon et al. | |
| 6,468,299 B2 | 10/2002 | Stack et al. | 7,090,694 B1 | 8/2006 | Morris et al. | |
| 6,485,510 B1 | 11/2002 | Camrud et al. | 7,101,840 B2 | 9/2006 | Brocchini et al. | |
| 6,488,694 B1 | 12/2002 | Lau et al. | 7,141,063 B2 | 11/2006 | White et al. | |
| 6,488,702 B1 | 12/2002 | Besselink | 7,147,655 B2 | 12/2006 | Chermoni | |
| 6,511,468 B1 | 1/2003 | Cragg et al. | 7,147,656 B2 | 12/2006 | Andreas et al. | |
| 6,520,986 B2 | 2/2003 | Martin et al. | 7,182,779 B2 | 2/2007 | Acosta et al. | |
| 6,520,987 B1 | 2/2003 | Plante | 7,192,440 B2 | 3/2007 | Andreas et al. | |
| 6,527,789 B1 | 3/2003 | Lau et al. | 7,220,755 B2 | 5/2007 | Betts et al. | |
| 6,527,799 B2 | 3/2003 | Shanley | 7,270,668 B2 | 9/2007 | Andreas et al. | |
| 6,530,944 B2 | 3/2003 | West et al. | 7,294,146 B2 | 11/2007 | Chew et al. | |
| 6,540,777 B2 | 4/2003 | Stenzel | 7,314,480 B2 | 1/2008 | Eidenschink et al. | |
| 6,551,350 B1 | 4/2003 | Thornton et al. | 7,320,702 B2 | 1/2008 | Hammersmark et al. | |
| 6,555,157 B1 | 4/2003 | Hossainy | 7,323,006 B2 | 1/2008 | Andreas et al. | |
| 6,569,180 B1 | 5/2003 | Sirhan et al. | 7,534,449 B2 | 5/2009 | Saltzman et al. | |
| 6,575,993 B1 | 6/2003 | Yock | 2001/0020154 A1 | 9/2001 | Bigus et al. | |
| 6,579,305 B1 | 6/2003 | Lashinski | 2001/0020173 A1 | 9/2001 | Klumb et al. | |
| 6,579,309 B1 | 6/2003 | Loos et al. | 2001/0020181 A1 | 9/2001 | Layne | |
| 6,582,394 B1 | 6/2003 | Reiss et al. | 2001/0035902 A1 | 11/2001 | Iddan et al. | |
| 6,582,460 B1 | 6/2003 | Cryer | 2001/0044595 A1 | 11/2001 | Reydel et al. | |
| 6,585,756 B1 | 7/2003 | Strecker | 2001/0044632 A1 | 11/2001 | Daniel et al. | |
| 6,592,549 B2 | 7/2003 | Gerdts et al. | 2001/0049547 A1 | 12/2001 | Moore | |
| 6,599,296 B1 | 7/2003 | Gillick et al. | 2002/0037358 A1 | 3/2002 | Barry et al. | |
| 6,599,314 B2 | 7/2003 | Mathis | 2002/0052642 A1 | 5/2002 | Cox et al. | |
| 6,602,226 B1 | 8/2003 | Smith et al. | 2002/0091439 A1 | 7/2002 | Baker et al. | |
| 6,602,282 B1 | 8/2003 | Yan | 2002/0092536 A1 | 7/2002 | LaFontaine et al. | |
| 6,605,062 B1 | 8/2003 | Hurley et al. | 2002/0107560 A1 | 8/2002 | Richter | |
| 6,605,109 B2 | 8/2003 | Fiedler | 2002/0111671 A1 | 8/2002 | Stenzel | |
| 6,607,553 B1 | 8/2003 | Healy et al. | 2002/0123786 A1 | 9/2002 | Gittings et al. | |
| 6,629,992 B2 | 10/2003 | Bigus et al. | 2002/0128706 A1 | 9/2002 | Osypka | |
| 6,645,517 B2 | 11/2003 | West | 2002/0138132 A1 | 9/2002 | Brown | |
| 6,645,547 B1 | 11/2003 | Shekalim et al. | 2002/0151924 A1 | 10/2002 | Shiber | |
| 6,656,212 B2 | 12/2003 | Ravenscroft et al. | 2002/0151955 A1 | 10/2002 | Tran et al. | |
| 6,660,031 B2 | 12/2003 | Tran et al. | 2002/0156496 A1 | 10/2002 | Chermoni | |
| 6,660,381 B2 | 12/2003 | Halas et al. | 2002/0168317 A1 | 11/2002 | Daighighian et al. | |
| 6,663,660 B2 | 12/2003 | Dusbabek et al. | 2002/0177890 A1 | 11/2002 | Lenker | |
| 6,666,883 B1 | 12/2003 | Seguin et al. | 2002/0183763 A1 | 12/2002 | Callol et al. | |
| 6,676,693 B1 | 1/2004 | Belding et al. | 2002/0188343 A1 | 12/2002 | Mathis | |

| | | | | | | |
|---|---|---|---|---|---|---|
| 2002/0188347 | A1 | 12/2002 | Mathis | 2006/0282150 A1 | 12/2006 | Olson et al. |
| 2002/0193873 | A1 | 12/2002 | Brucker et al. | 2006/0287726 A1 | 12/2006 | Segal et al. |
| 2003/0045923 | A1 | 3/2003 | Bashiri et al. | 2007/0027521 A1 | 2/2007 | Andreas et al. |
| 2003/0093143 | A1 | 5/2003 | Zhao et al. | 2007/0067012 A1 | 3/2007 | George et al. |
| 2003/0097169 | A1 | 5/2003 | Brucker et al. | 2007/0088368 A1 | 4/2007 | Acosta et al. |
| 2003/0114912 | A1 | 6/2003 | Sequin et al. | 2007/0088420 A1 | 4/2007 | Andreas et al. |
| 2003/0114919 | A1 | 6/2003 | McQuiston et al. | 2007/0088422 A1 | 4/2007 | Chew et al. |
| 2003/0114922 | A1 | 6/2003 | Iwasaka et al. | 2007/0100423 A1 | 5/2007 | Acosta et al. |
| 2003/0125791 | A1 | 7/2003 | Sequin et al. | 2007/0100424 A1 | 5/2007 | Chew et al. |
| 2003/0125800 | A1 | 7/2003 | Shulze et al. | 2007/0106365 A1 | 5/2007 | Andreas et al. |
| 2003/0125802 | A1 | 7/2003 | Callol et al. | 2007/0118202 A1 | 5/2007 | Chermoni |
| 2003/0135259 | A1 | 7/2003 | Simso | 2007/0118203 A1 | 5/2007 | Chermoni |
| 2003/0135266 | A1 | 7/2003 | Chew et al. | 2007/0118204 A1 | 5/2007 | Chermoni |
| 2003/0139796 | A1 | 7/2003 | Sequin et al. | 2007/0156225 A1 | 7/2007 | George et al. |
| 2003/0139797 | A1 | 7/2003 | Johnson et al. | 2007/0156226 A1 | 7/2007 | Chew et al. |
| 2003/0139798 | A1 | 7/2003 | Brown et al. | 2007/0179587 A1 | 8/2007 | Acosta et al. |
| 2003/0163085 | A1 | 8/2003 | Tanner et al. | 2007/0219612 A1 | 9/2007 | Andreas et al. |
| 2003/0176909 | A1 | 9/2003 | Kusleika | 2007/0219613 A1 | 9/2007 | Kao et al. |
| 2003/0191516 | A1 | 10/2003 | Weldon et al. | 2007/0265637 A1 | 11/2007 | Andreas et al. |
| 2003/0195609 | A1 | 10/2003 | Berenstein | 2007/0270936 A1 | 11/2007 | Andreas et al. |
| 2003/0199821 | A1 | 10/2003 | Gerdts et al. | 2007/0276461 A1 | 11/2007 | Andreas et al. |
| 2003/0204238 | A1 | 10/2003 | Tedeschi | 2007/0281117 A1 | 12/2007 | Kaplan et al. |
| 2003/0212447 | A1 | 11/2003 | Euteneuer | 2007/0292518 A1 | 12/2007 | Ludwig |
| 2003/0225446 | A1 | 12/2003 | Hartley | 2008/0046067 A1 | 2/2008 | Toyokawa |
| 2004/0024450 | A1 | 2/2004 | Shulze et al. | 2008/0071345 A1 | 3/2008 | Hammersmark et al. |
| 2004/0030380 | A1 | 2/2004 | Shulze et al. | 2008/0077229 A1 | 3/2008 | Andreas et al. |
| 2004/0044395 | A1 | 3/2004 | Nelson | 2008/0091257 A1 | 4/2008 | Andreas et al. |
| 2004/0073290 | A1 | 4/2004 | Chouinard | 2008/0097299 A1 | 4/2008 | Andreas et al. |
| 2004/0087965 | A1 | 5/2004 | Levine et al. | 2008/0097574 A1 | 4/2008 | Andreas et al. |
| 2004/0093061 | A1 | 5/2004 | Acosta et al. | 2008/0132989 A1 | 6/2008 | Snow et al. |
| 2004/0093067 | A1 | 5/2004 | Israel | 2008/0147162 A1 | 6/2008 | Andreas et al. |
| 2004/0098081 | A1 | 5/2004 | Landreville et al. | 2008/0177369 A1 | 7/2008 | Will et al. |
| 2004/0106979 | A1 | 6/2004 | Goicoechea | 2008/0199510 A1 | 8/2008 | Ruane et al. |
| 2004/0111145 | A1 | 6/2004 | Serino et al. | 2008/0208311 A1 | 8/2008 | Kao et al. |
| 2004/0117008 | A1 | 6/2004 | Wnendt et al. | 2008/0208318 A1 | 8/2008 | Kao et al. |
| 2004/0176832 | A1 | 9/2004 | Hartley et al. | 2008/0234795 A1 | 9/2008 | Snow et al. |
| 2004/0181239 | A1 | 9/2004 | Dorn et al. | 2008/0234798 A1 | 9/2008 | Chew et al. |
| 2004/0186551 | A1 | 9/2004 | Kao et al. | 2008/0234799 A1 | 9/2008 | Acosta et al. |
| 2004/0193245 | A1 | 9/2004 | Deem et al. | 2008/0269865 A1 | 10/2008 | Snow et al. |
| 2004/0215165 | A1 | 10/2004 | Coyle et al. | 2009/0076584 A1 | 3/2009 | Mao et al. |
| 2004/0215312 | A1 | 10/2004 | Andreas | 2009/0105686 A1 | 4/2009 | Snow et al. |
| 2004/0243217 | A1 | 12/2004 | Andersen et al. | 2009/0149863 A1 | 6/2009 | Andreas et al. |
| 2004/0249434 | A1 | 12/2004 | Andreas et al. | 2009/0234428 A1 | 9/2009 | Snow et al. |
| 2004/0249435 | A1 | 12/2004 | Andreas et al. | 2009/0264979 A1 | 10/2009 | Kao et al. |
| 2005/0010276 | A1 | 1/2005 | Acosta et al. | 2010/0004729 A1 | 1/2010 | Chew et al. |
| 2005/0038494 | A1 | 2/2005 | Eidenschink | | | |
| 2005/0038505 | A1 | 2/2005 | Shuize et al. | FOREIGN PATENT DOCUMENTS | | |
| 2005/0049673 | A1 | 3/2005 | Andreas et al. | DE 196 30 469 | 1/1998 | |
| 2005/0080474 | A1 | 4/2005 | Andreas et al. | DE 199 50 756 | 8/2000 | |
| 2005/0080475 | A1 | 4/2005 | Andreas et al. | DE 101 03 000 | 8/2002 | |
| 2005/0090846 | A1 | 4/2005 | Pedersen et al. | EP 203945 B2 | 12/1986 | |
| 2005/0125051 | A1 | 6/2005 | Eidenschink et al. | EP 274129 B1 | 7/1988 | |
| 2005/0131008 | A1 | 6/2005 | Betts et al. | EP 282143 | 9/1988 | |
| 2005/0133164 | A1 | 6/2005 | Fischer et al. | EP 0 364 787 | 4/1990 | |
| 2005/0143827 | A1 | 6/2005 | Globerman et al. | EP 0 505 686 | 9/1992 | |
| 2005/0149159 | A1 | 7/2005 | Andreas et al. | EP 0533 960 | 3/1993 | |
| 2005/0165378 | A1 | 7/2005 | Heinrich et al. | EP 0 714 640 | 6/1996 | |
| 2005/0209674 | A1 | 9/2005 | Kutscher et al. | EP 0 596 145 | 5/1997 | |
| 2005/0222671 | A1 | 10/2005 | Schaeffer et al. | EP 947180 | 10/1999 | |
| 2005/0228477 | A1 | 10/2005 | Grainger et al. | EP 1 258 230 | 11/2002 | |
| 2005/0245637 | A1 | 11/2005 | Hossainy et al. | EP 1 277 449 | 1/2003 | |
| 2005/0288763 | A1 | 12/2005 | Andreas et al. | EP 1 290 987 | 3/2003 | |
| 2005/0288764 | A1 | 12/2005 | Snow et al. | EP 1 318 765 | 6/2003 | |
| 2005/0288766 | A1 | 12/2005 | Plain et al. | EP 1 470 834 | 10/2004 | |
| 2006/0069424 | A1 | 3/2006 | Acosta et al. | EP 1 523 959 A2 | 4/2005 | |
| 2006/0200223 | A1 | 9/2006 | Andreas et al. | EP 1 523 960 A2 | 4/2005 | |
| 2006/0206190 | A1 | 9/2006 | Chermoni | EP 1266638 B1 | 10/2005 | |
| 2006/0229700 | A1 | 10/2006 | Acosta et al. | JP 03-133446 | 6/1991 | |
| 2006/0229706 | A1 | 10/2006 | Shulze et al. | JP 10-503663 | 4/1998 | |
| 2006/0271150 | A1 | 11/2006 | Andreas et al. | JP 10-295823 | 11/1998 | |
| 2006/0271151 | A1 | 11/2006 | McGarry et al. | JP 11-503056 T | 3/1999 | |
| 2006/0282147 | A1 | 12/2006 | Andreas et al. | JP 2001-190687 | 7/2001 | |
| 2006/0282149 | A1 | 12/2006 | Kao | | | |

| | | |
|---|---|---|
| JP | 2002-538932 T | 11/2002 |
| WO | WO 95/26695 A2 | 10/1995 |
| WO | WO 95/29647 | 11/1995 |
| WO | WO 96/26689 | 9/1996 |
| WO | WO 96/33677 | 10/1996 |
| WO | WO 96/39077 | 12/1996 |
| WO | WO 97/10778 | 3/1997 |
| WO | WO 97/46174 | 12/1997 |
| WO | WO 97/48351 | 12/1997 |
| WO | WO 98/20810 | 5/1998 |
| WO | WO 98/37833 | 9/1998 |
| WO | WO 98/58600 | 12/1998 |
| WO | WO 99/01087 A1 | 1/1999 |
| WO | WO 99/65421 | 12/1999 |
| WO | WO 00/12832 A3 | 3/2000 |
| WO | WO 00/15151 | 3/2000 |
| WO | WO 00/25841 | 5/2000 |
| WO | WO 00/32136 | 6/2000 |
| WO | WO 00/41649 A1 | 7/2000 |
| WO | WO 00/50116 | 8/2000 |
| WO | WO 00/56237 | 9/2000 |
| WO | WO 00/62708 | 10/2000 |
| WO | WO 00/72780 | 12/2000 |
| WO | WO 01/26707 | 4/2001 |
| WO | WO 01/34063 | 5/2001 |
| WO | WO 01/70297 | 9/2001 |
| WO | WO 01/91918 | 12/2001 |
| WO | WO 02/085253 | 10/2002 |
| WO | WO 02/098326 | 12/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |
| WO | WO 2004/087006 | 10/2004 |
| WO | WO 2005/009295 | 2/2005 |
| WO | WO 2005/013853 | 2/2005 |
| WO | WO 2005/023153 | 3/2005 |
| WO | WO 2006/036939 | 4/2006 |
| WO | WO 2006/047520 | 5/2006 |
| WO | WO 2007/035805 | 3/2007 |
| WO | WO 2007/053187 | 5/2007 |
| WO | WO 2007/146411 | 12/2007 |
| WO | WO 2008/005111 | 1/2008 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al, Parallel Production of Oligonucleotide Arrays Using Membranes and Reagent Jet Printing, BioTechniques 25:886-890 (Nov. 1998).

Supplementary European Search Report of EP Patent Application No. 04780248.3, dated Feb. 20, 2007, 4 pages total.

Supplementary European Search Report of EP Patent Application No. 04780248.3, dated May 3, 2007, 5 pages total.

"Drug Delivery Stent With Holes Located on Neutral Axis" Research Disclosure, Kenneth Mason Publications, Hampshire, CB, No. 429, Jan. 2000, p. 13, XP00976354.

Evans Analytical Group, "Functional Sites on Non-polymeric Materials: Gas Plasma Treatment and Surface Analysis," http://www.eaglabs.com.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

European Search Report and Search Opinion of EP Patent Application No. 09175432.5, mailed Dec. 17, 2009, 8 pages total.

\* cited by examiner

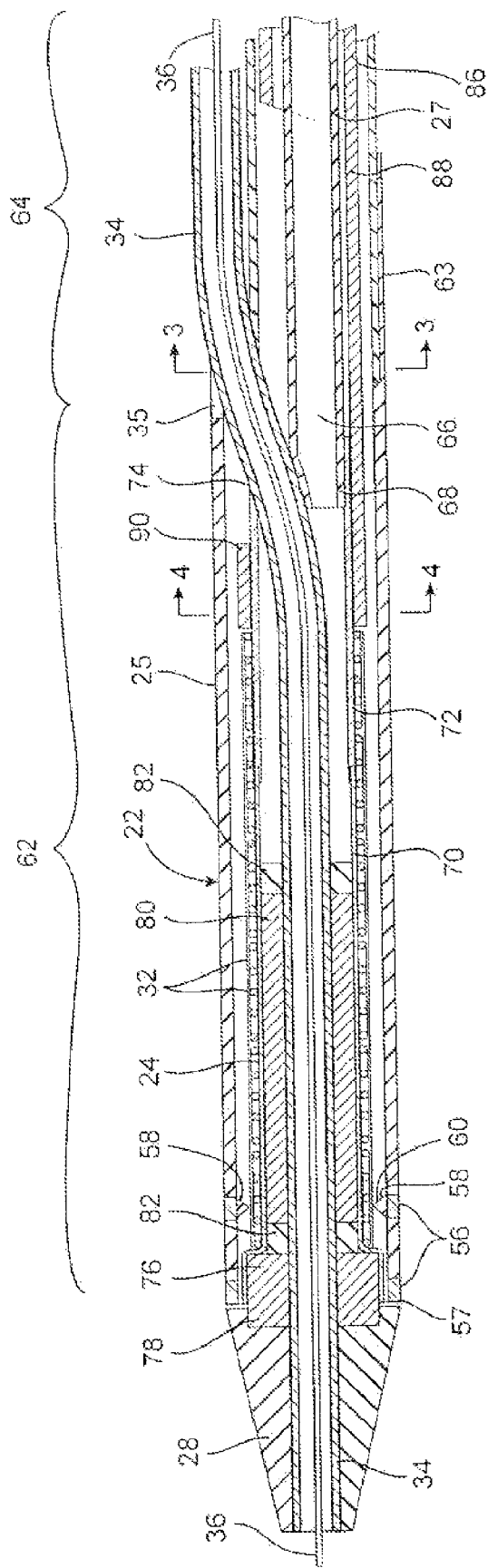
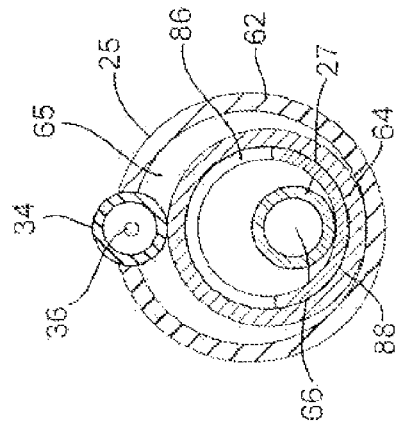
FIG. 2A
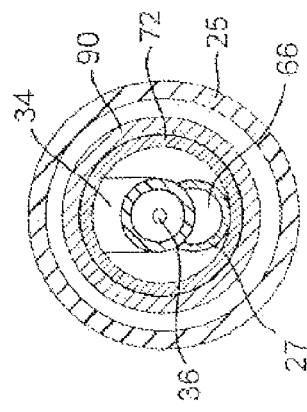
FIG. 3
FIG. 4

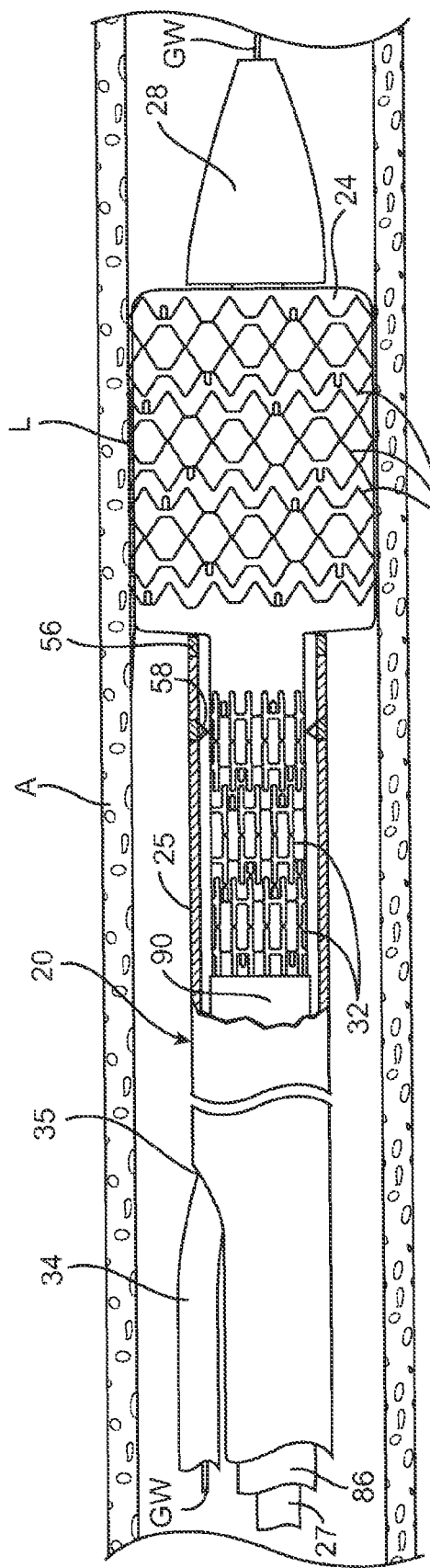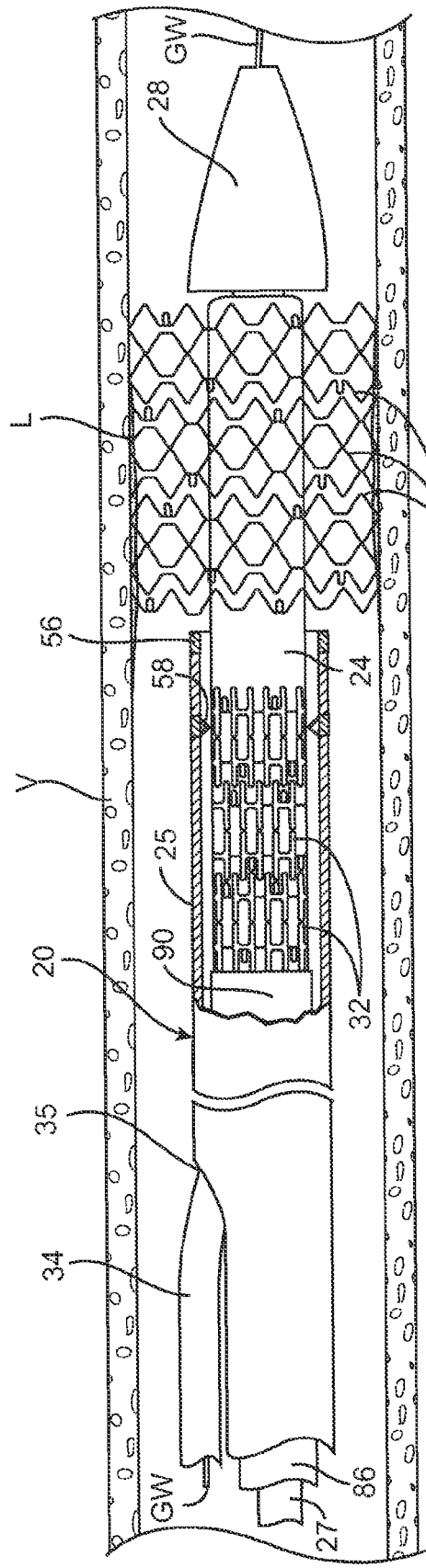

APPARATUS AND METHODS FOR DEPLOYMENT OF VASCULAR PROSTHESES

CROSS-REFERENCES TO RELATED APPLICATIONS

This application is a continuation of co-pending application Ser. No. 10/637,713 filed Aug. 8, 2003 which is a continuation-in-part of co-pending application Ser. No. 10/412,714, filed Apr. 10, 2003, which is a continuation-in-part of application Ser. No. 10/306,813, filed Nov. 27, 2002, which is a non-provisional of provisional application Ser. No. 60/336,767, filed Dec. 3, 2001, and a non-provisional of provisional application Ser. No. 60/364,389, filed Mar. 13, 2002, the full disclosures of which are incorporated herein by reference.

BACKGROUND OF THE INVENTION

1. Field of Invention

This invention relates generally to vascular catheters, and more specifically to stents and stent delivery catheters for deployment in the coronary arteries and other vessels.

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. However, in recent years, improvements in stent design and the advent of drug-eluting stents have reduced restenosis rates dramatically. As a result, the number of stenting procedures being performed in the United States, Europe, and elsewhere has soared.

Stents are delivered to the coronary arteries using long, flexible vascular catheters typically inserted through a femoral artery. For self-expanding stents, the stent is simply released from the delivery catheter and it resiliently expands into engagement with the vessel wall. For balloon expandable stents, a balloon on the delivery catheter is expanded which expands and deforms the stent to the desired diameter, whereupon the balloon is deflated and removed.

Current stent delivery technology, however, suffers from a number of drawbacks. For example, current stent delivery catheters are not capable of customizing the length of the stent in situ to match the size of the lesion to be treated. While lesion size may be measured prior to stenting using angiography or fluoroscopy, such measurements may be inexact. If a stent is introduced that is found to be of inappropriate size, the delivery catheter and stent must be removed from the patient and replaced with a different device of correct size.

Moreover, current stent delivery devices cannot treat multiple lesions with a single catheter. Current devices are capable of delivering only a single stent with a single catheter, and if multiple lesions are to be treated, a new catheter and stent must be introduced for each lesion to be treated.

Further, current stent delivery devices are not well-adapted for treating vascular lesions that are very long and/or in curved regions of a vessel. Current stents have a discrete length that is relatively short due to their stiffness. If current stents were made longer so as to treat longer lesions, they would not conform well to the curvature of vessels or to the movement of vessels on the surface of the beating heart. On the other hand, any attempt to place multiple stents end-to-end in longer lesions is hampered by the inability to maintain appropriate inter-stent spacing and to prevent overlap of adjacent stents.

Additionally, some stent delivery catheters and angioplasty balloon catheters, particularly those having movable external sheaths to enclose the stent or balloon, suffer from poor tracking and cumbersome interaction with guidewires. Some such catheters utilize an "over-the-wire" design in which the guidewire extends through an inner lumen of the catheter from its proximal end to its distal end, a design that makes catheter exchanges cumbersome and time-consuming. Rapid exchange designs have also been proposed for such catheters wherein the guidewire extends through the distal end of the catheter and out through a port in a sidewall of the sheath. However, in these designs the guidewire inhibits smooth retraction of the sheath and, if the sheath is retracted a substantial distance, the port can become so displaced from the distal end of the catheter that the guidewire does not slide smoothly as the catheter is moved.

Finally, many stent delivery catheters suffer from inflexibility and high cross-sectional profile, which hamper endovascular positioning.

For these and other reasons, stents and stent delivery catheters are needed which enable the customization of stent length in situ, and the treatment of multiple lesions of various sizes, without requiring removal of the delivery catheter from the patient. Such stents and stent delivery catheters should be capable of treating lesions of particularly long length and lesions in curved regions of a vessel, and should be highly flexible to conform to vessel shape and movement. Such stent delivery catheters should further be of minimal cross-sectional profile and should be highly flexible for endovascular positioning through tortuous vascular pathways.

BRIEF SUMMARY OF THE INVENTION

The invention provides apparatus and methods for delivering prostheses or stents into body lumens. In one aspect of the invention, an apparatus for delivering a prosthesis into a target vessel comprises a flexible catheter shaft having proximal and distal ends and a first lumen therein. A tubular prosthesis is releasably carried near the distal end of the catheter shaft and is expandable to a shape suitable for engaging the target vessel. A sheath is disposed over the catheter shaft and the tubular prosthesis and is axially movable relative thereto. The sheath has proximal and distal ends, a sidewall, and an exit port in the sidewall between the proximal and distal ends. A guidewire tube extends through the exit port and has a distal extremity disposed within the tubular prosthesis and a proximal extremity disposed outside of the sheath, the guidewire tube being adapted for slidably receiving a guidewire therethrough.

Preferably, the guidewire tube is slidable through the exit port so that the sheath slides relative to the guidewire tube as it is retracted to expose the prosthesis for deployment. In one embodiment, the exit port is fluidly sealed around the guidewire tube so as to limit the introduction of blood into the interior of the sheath and limit the flow of flushing fluids from within the sheath into the vessel. Usually the guidewire tube is fixed relative to the catheter shaft, and may be attached thereto. If an expandable member is mounted to the catheter shaft for prosthesis expansion, the guidewire tube may extend through and attach to the expandable member.

Because the guidewire tube exits the sheath in a distal extremity thereof, the sheath has a low profile portion proximal to the exit port that has a smaller diameter than the portion distal to the exit port. Not only does this reduce the cross-sectional profile, but increases the flexibility of the device.

The exit port may be cut into the sidewall of the sheath to face laterally, or alternatively oriented so as to face generally in a proximal direction. The exit port is usually positioned so as to be closer to the distal end of the sheath than to the proximal end thereof, and is preferably a distance of about 20-35 cm from the distal end of the sheath. With the sheath advanced fully distally over the catheter shaft, the proximal extremity of the guidewire lumen exposed outside the sheath is preferably about 3-15 cm in length, although various lengths are possible, even as long or longer than the catheter shaft itself. The proximal end of the guidewire tube is preferably disposed a distance of less than about one-half the length of the catheter shaft from the distal end thereof, but in some embodiments may extend further proximally, even as far as the proximal end of the catheter shaft.

The apparatus of the invention may be configured to deliver tubular prostheses that are either self-expanding or expandable by a balloon or other expandable member. When self-expanding prostheses are used, the sheath is adapted to constrain the prosthesis in a collapsed configuration. Upon retraction of the sheath, the prosthesis is released and self-expands to engage the vessel.

For balloon-expandable prostheses, an expandable member is mounted to the catheter shaft near the distal end thereof. The tubular prosthesis is positionable over the expandable member for expansion therewith. Usually the expandable member will comprise a balloon in communication with an inflation lumen in the catheter shaft for delivery of inflation fluid to the balloon. The sheath is axially positionable relative to the expandable member and configured to restrain expansion of a selected portion of the expandable member. Preferably the sheath is reinforced to prevent expansion thereof by the expandable member.

In a preferred aspect of the invention, the tubular prosthesis comprises a plurality of prosthesis segments. The sheath is axially movable relative to the prosthesis segments and configured to restrain expansion of a selectable number of prosthesis segments. In this way, lesions of various lengths may be treated by adjusting the length of the prosthesis in situ, without removal of the device from the body. In these embodiments, a pusher may be slidably disposed over the catheter shaft within the sheath. The pusher has a distal end in engagement with the tubular prosthesis for moving the tubular prosthesis relative to the catheter shaft.

In a further aspect of the invention, a method of delivering a prosthesis in a target vessel of a patient comprises inserting a guidewire through the patient's vasculature to the target vessel; slidably coupling a delivery catheter to the guidewire, the delivery catheter having a sheath and a guidewire tube, a proximal extremity of the guidewire tube being outside the sheath and a distal extremity of the guidewire tube being inside the sheath, the guidewire being slidably positioned through the guidewire tube; advancing the delivery catheter over the guidewire to the target vessel; retracting the sheath relative to the guidewire tube to expose a tubular prosthesis carried by the delivery catheter; and expanding the tubular prosthesis into engagement with the target vessel.

Usually, the guidewire tube will extend through an exit port in the sheath, and the guidewire tube will slide through the exit port as the sheath is retracted. Optionally, the method may include sealing the exit port around the guidewire tube to restrict fluid flow therethrough.

In a preferred embodiment, an expandable member is fixed to a catheter shaft over which the sheath is disposed, and the tubular prosthesis is positionable over the expandable member. The tubular prosthesis will then be expanded by expanding the expandable member. The sheath may be used to cover a proximal portion of the expandable member to constrain the proximal portion from expansion while a distal portion of the expandable member expands. Usually, the expandable member is inflatable and will be inflated by delivering inflation fluid to the expandable member through an inflation lumen in the catheter shaft. The guidewire tube preferably extends through the interior of the expandable member, which may be attached to the guidewire tube.

In a preferred aspect of the invention, the tubular prosthesis comprises a plurality of prosthesis segments, and the method includes positioning a first selected number of the prosthesis segments on the expandable member for expansion therewith. The method may further include positioning the sheath over a second selected number of the prosthesis segments to constrain expansion thereof. The first selected number of prosthesis segments may be positioned on the expandable member by pushing the first selected number with a pusher that is axially slidable relative to the expandable member.

In alternative embodiments, the tubular prosthesis self-expands when the sheath is retracted. In embodiments in which the prosthesis comprises multiple prosthesis segments, the sheath may be retracted relative to a selected number of such segments to allow the segments to self-expand into contact with the vessel.

In another aspect, the invention provides a balloon catheter for treating a target vessel that includes a flexible catheter shaft having proximal and distal ends and a first lumen therein. An expandable member is connected to the catheter shaft, and a sheath is disposed over the catheter shaft and the expandable member and is axially movable relative thereto. The sheath has an exit port in a sidewall thereof between its proximal and distal ends. A guidewire tube extends through the exit port and has a proximal extremity disposed outside of the sheath and a distal extremity disposed within the sheath that is coupled to the catheter shaft or the expandable member. The guidewire tube is adapted for slidably receiving a guidewire therethrough. The expandable member preferably comprises a balloon in fluid communication with the first lumen to receive inflation fluid therefrom. The sheath may be positionable to constrain a first selected portion of the expandable member from expansion while a second selected portion of the expandable member expands.

In a preferred embodiment of the balloon catheter of the invention, a tubular prosthesis is disposed on the expandable member and is expandable therewith. The tubular prosthesis will preferably comprise a plurality of unconnected stent segments that are slidable relative to the expandable member. The sheath is positionable to expose a first selected portion of the stent segments while covering a second selected portion of the stent segments.

In yet another aspect of the invention, an apparatus for delivering a prosthesis into a target vessel comprises a flexible catheter shaft having proximal and distal ends and a tubular prosthesis slidably coupled to the catheter shaft, the tubular prosthesis being expandable to a shape suitable for engaging the target vessel. A pusher is provided for moving the tubular prosthesis from a pre-deployment position to a deployment position near the distal end of the catheter shaft. The apparatus further includes a stop on the catheter shaft configured to engage the tubular prosthesis when the tubular prosthesis is in the deployment position.

In one embodiment, an expandable member is coupled to the catheter shaft and the tubular prosthesis is adapted for expansion by the expandable member. The expandable member, e.g. balloon, has an interior, and the stop is preferably disposed within the interior of the expandable member. Alternatively, the tubular prosthesis is self-expanding and expands upon being released from the catheter shaft.

In a preferred aspect, a plurality of tubular prostheses are slidably coupled to the catheter shaft and are movable by the pusher to the deployment position. In addition, a sheath may be movably coupled to the catheter shaft and positionable over the tubular prosthesis or prostheses.

In a further method of deploying a tubular prosthesis in a target vessel according to the invention a catheter shaft is positioned in a target vessel and the tubular prosthesis is moved distally relative to the catheter shaft while the catheter shaft remains in the target vessel until the prosthesis engages a stop near the distal end of the catheter shaft. The tubular prosthesis is then expanded to engage a wall of the target vessel.

After expanding the tubular prosthesis, a second prosthesis (or any number of additional prostheses) may be moved distally relative to the catheter shaft until the second prosthesis engages the stop, and the second prosthesis then expanded to engage a wall of the target vessel. Alternatively, a second prosthesis may be moved distally relative to the catheter shaft simultaneously with moving the tubular prosthesis, and both the second prosthesis and the tubular prosthesis are expanded together to engage the wall of the target vessel. Usually, the tubular prosthesis and any additional prostheses are moved by a pusher movably coupled to the catheter shaft.

The tubular prosthesis is preferably expanded by inflating a balloon coupled to the catheter shaft. Alternatively, the tubular prosthesis may be self-expandable.

Further, the method may include retaining a second prosthesis in an unexpanded configuration on the catheter shaft while the tubular prosthesis is expanded. In one embodiment, the second prosthesis is retained within a sheath movably coupled to the catheter shaft.

Further aspects of the nature and advantages of the invention will become apparent from the detailed description below taken in conjunction with the drawings.

BRIEF DESCRIPTION OF THE DRAWINGS

FIG. 2A is a side cross-section of a distal portion of the stent delivery catheter of FIG. 1 with expandable member deflated and sheath advanced distally.

FIG. 3 is a transverse cross-section through line 3-3 of FIG. 2A.

FIG. 4 is a transverse cross-section through line 4-4 of FIG. 2A.

FIGS. 7A-7E are side cut-away views of the stent delivery catheter of the invention positioned in a vessel with the stent segments of FIGS. 5A-5B, illustrating various steps of delivering a prosthesis according to the method of the invention.

DETAILED DESCRIPTION OF THE INVENTION

Figure 1:
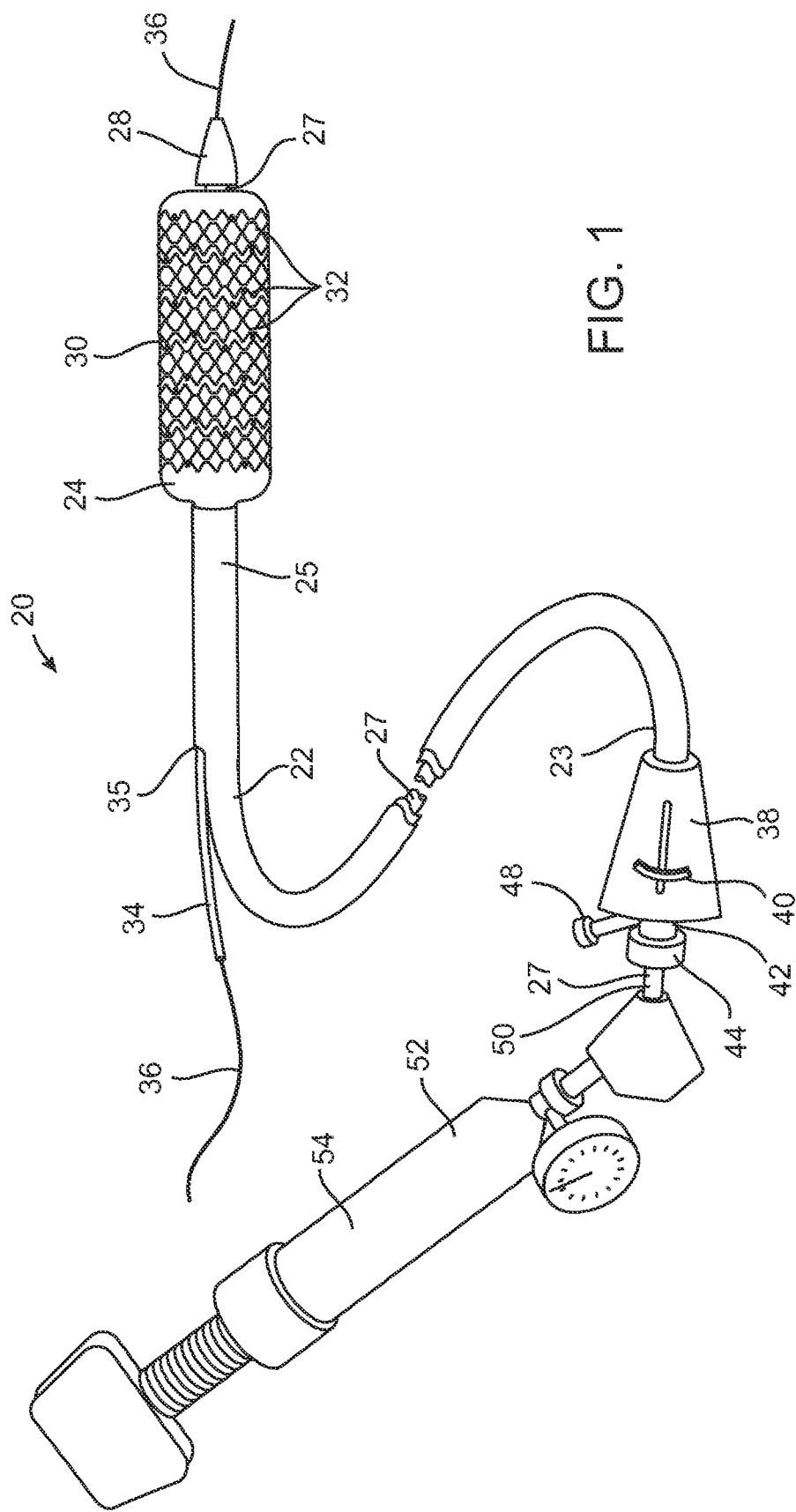
FIG. 1 is a perspective view of a stent delivery catheter according to the invention with sheath retracted and expandable member inflated.

A first embodiment of a stent delivery catheter according to present invention is illustrated in FIG. 1. Stent delivery catheter 20 includes a catheter body 22 comprising an outer sheath 25 slidably disposed over an inner shaft 27. An expandable member 24, preferably an inflatable balloon (shown in an inflated configuration), is mounted to inner shaft 27 and is exposed by retracting sheath 25 relative to inner shaft 27. A tapered nosecone 28, composed of a soft elastomeric material to reduce trauma to the vessel during advancement of the device, is mounted distally of expandable member 38. A stent 30, which preferably comprises a plurality of separate or separable stent segments 32, is disposed on expandable member 24 for expansion therewith. A guidewire tube 34 is slidably positioned through a guidewire tube exit port 35 in sheath 25 proximal to expandable member 24. A guidewire 36 is positioned slidably through guidewire tube 34, expandable member 24, and nosecone 28 and extends distally thereof.

A handle 38 is mounted to a proximal end 23 of sheath 25 and includes an actuator 40 slidably mounted thereto for purposes described below. An adaptor 42 is mounted to the proximal end of handle 38 and provides a catheter port 44 through which inner shaft 27 is slidably positioned. A flush port 48 is mounted to the side of adaptor 42 through which a fluid such as saline can be introduced into the interior of catheter body 22. An annular seal (not shown) in catheter port 44 seals around inner shaft 27 to prevent fluid from leaking through catheter port 44. Optionally, a clamp (not shown) such as a threaded collar, can be mounted to catheter port 44 to lock inner shaft 27 relative to handle 38.

Inner shaft 27 has a proximal end 50 to which is mounted an inflation adaptor 52. Inflation adaptor 52 is configured to be fluidly coupled to an inflation device 54, which may be any commercially available balloon inflation device such as those sold under the trade name "Indeflator™," available from Advanced Cardiovascular Systems of Santa Clara, Calif. Inflation adaptor 52 is in fluid communication with expandable member 24 via an inflation lumen (described below) in inner shaft 27 to enable inflation of expandable member 24.

Referring now to FIGS. 2A-2B, 3 and 4, which show a distal portion of the stent delivery catheter in cross-section, it may be seen that sheath 25 may be extended up to nosecone 28 to fully surround expandable member 24 and stent segments 32. One or more radiopaque markers 56 are mounted near a distal end 57 of sheath 25 to facilitate visualization of the position of sheath 25 using fluoroscopy. In a preferred embodiment, two annular markers 56 are spaced apart a length equal to the length of one of stent segments 32 for purposes described more fully below. Sheath 25 further includes a valve member 58 preferably spaced proximally from distal end 57 a distance equal to the length of one of stent segments 32. Valve member 58 has an inwardly extending flange 60 configured to frictionally engage stent segments 32 and thereby restrict the sliding movement of stent segments 32 distally relative to sheath 25. Flange 60 may be a polymeric material integrally formed with sheath 25 or a separate annular member bonded or otherwise mounted to sheath 25. Various embodiments of valve member 58 are described in copending application Ser. No. 10/412,714, Filed Apr. 10, 2003, which is incorporated herein by reference.

Sheath 25 has a distal extremity 62 configured to surround expandable member 24 and stent segments 32 disposed thereon when in an unexpanded configuration. Distal extremity 62 extends proximally to a junction 63, preferably aligned with the location of guidewire tube exit port 35, where distal extremity 62 is joined to a proximal extremity 64 that extends proximally to handle 38 (see FIG. 1). In a preferred embodiment, distal extremity 62 has a length of about 15-35 cm and proximal extremity 64 as a length of about 100-125 cm. Proximal extremity 64 may be constructed of a variety of biocompatible polymers or metals, preferably being stainless steel or Nitinol. Distal extremity 62 may be a polymer such as PTFE, FEP, polyimide, or Pebax, and is preferably reinforced with a metallic or polymeric braid to resist radial expansion when expandable member 24 is expanded.

Preferably, proximal extremity 64 has a smaller transverse dimension than distal extremity 62 to accommodate the added width of guidewire tube 34 within the vessel lumen, as well as to maximize flexibility and minimize profile. In one embodiment, shown in FIG. 3, distal extremity 62 is a tubular member having a first outer diameter, preferably about 1.0-1.5 mm, and proximal extremity 64 is a tubular member having a second, smaller outer diameter, preferably about 0.7-1.0 mm. At the junction of proximal extremity 64 with distal extremity 62, a proximally-facing crescent-shaped opening 65 is formed between the two tubular members that creates guidewire tube exit port 35. Excess space within crescent-shaped opening 65 may be filled with a filler material such as adhesive.

In an alternative embodiment (not shown), a hole is formed in the sidewall of distal extremity 62 or proximal extremity 64 to create guidewire tube exit port 35. Proximally of guidewire tube exit port 35, the wall of sheath 25 adjacent to guidewire tube 34 is flattened or collapsible inwardly thereby reducing the transverse dimension of sheath 25 to accommodate the width of guidewire tube 34.

Guidewire tube 34 is slidably positioned through guidewire tube exit port 35. Preferably, guidewire tube exit port 35 is configured to provide a total or partial fluid seal around the periphery of guidewire tube 34 to limit blood flow into the interior of sheath 25 and to limit leakage of saline (or other flushing fluid) out of sheath 25. This may be accomplished by sizing guidewire tube exit port 35 appropriately so as to form a fairly tight frictional seal around guidewire tube 34 while still allowing the sliding motion thereof relative to sheath 25. Alternatively an annular sealing ring may be mounted in guidewire tube exit port 35 to provide the desired seal.

Guidewire tube exit port 35 will be positioned to provide optimal tracking of stent delivery catheter 20 through the vasculature and maximizing the ease with which the catheter can be inserted onto and removed from a guidewire to facilitate catheter exchanges. Usually, guidewire tube exit port 35 will be positioned at a location proximal to expandable member 24 when sheath 25 is extended fully distally up to nosecone 28, but a distance of no more than one-half the length of sheath 25 from distal end 57. In preferred embodiments for coronary applications, guidewire tube exit port 35 is spaced proximally a distance of about 20-35 cm from the distal end 57 of sheath 25.

Guidewire tube 34 should extend proximally from guidewire tube exit port 35 a distance at least as long as the longest possible stent that may be deployed, e.g. 30-60 mm, to allow for retraction of sheath 25 that distance while retaining a portion of guidewire tube 34 external to sheath 25. Preferably guidewire tube 34 extends proximally a distance of about 3-15 cm from guidewire tube exit port 35 when sheath 25 is in a fully distal position, with the proximal end thereof disposed a distance of about 23-50 cm from the distal tip of nosecone 28. Where stent delivery catheter 20 is to be positioned through a guiding catheter, the proximal end of guidewire tube 34 will preferably be positioned so as to be within the guiding catheter when expandable member 24 is positioned at the target site for stent deployment. Guidewire tube 34 is preferably a highly flexible polymer such as PTFE, FEP, polyimide, or Pebax, and may optionally have a metal or polymer braid embedded in it to increase kink-resistance.

Inner shaft 27 forms an inflation lumen 66 that is in communication with interior of expandable member 24. In the distal extremity of stent delivery catheter 20 inner shaft 27 is preferably formed of a polymer such as PTFE, FEP, polyimide, or Pebax, and may be reinforced with a metallic braid for added radial strength and kink resistance. In the proximal extremity of delivery catheter 20, inner shaft 27 may be a similar polymer or a metal such as stainless steel or Nitinol.

Expandable member 24 has an expandable balloon member 70 that is joined to a non-expandable tubular leg 72. Expandable balloon member 70 is a semi-compliant polymer such as Pebax or Nylon. Tubular leg 72 is preferably a polymer such as polyimide, PTFE, FEP or Pebax and may optionally be reinforced with a metal or polymer braid. Tubular leg 72 has an open proximal end 74 through which guidewire tube 34 extends. Proximal end 74 of tubular leg 72 is fixed to distal end 68 of inner shaft 27 and to guidewire tube 34, forming a fluid-tight seal. Balloon member 70 has a distal end 76 bonded to an annular stop 78, which is mounted to nosecone 28. Stop 78 has a size and shape selected to engage stent segment 32 and provide a stop against which stent segments 32 can be located in the ideal deployment position without being pushed beyond the distal end of balloon member 70. Guidewire tube 34 passes through the interior of balloon member 70 and is mounted to nosecone 28, thereby providing a passage through the distal portion of catheter body 22 through which guidewire 36 may pass.

Optionally, within the interior of balloon member 70 an annular base member 80 is mounted to guidewire tube 34 and has a diameter selected to urge balloon member 70 against stent segments 32 in their unexpanded configuration, thereby providing frictional engagement with stent segments 32. This helps to limit unintended sliding movement of stent segments 32 on balloon member 70. Base member 80 may be made of a soft elastomer, foam, or other compressible material. Adjacent to the distal and proximal ends of base member 80 two annular radiopaque markers 82 are mounted to guidewire tube 34, facilitating visualization of the location of balloon member 70 with fluoroscopy and enabling appropriate positioning of stent segments 32 on balloon member 70. Alternatively, only a single marker 82 at the distal end of base member 80 may be used, or markers may be placed at other locations on nosecone 28, guidewire tube 34, or inner shaft 27. Such markers may be made of various radiopaque materials such as platinum/iridium, tantalum, and other materials.

Stent segments 32 are slidably positioned over balloon member 70. Depending upon the number of stent segments 32 loaded in stent delivery catheter 20, stent segments 32 may be positioned over both balloon member 70 and tubular leg 72. In an exemplary embodiment, each stent segment is about 2-8 mm in length, and up to 10-50 stent segments may be positioned end-to-end in a line over balloon member 70 and tubular leg 72. Stent segments 32 preferably are in direct contact with each other, but alternatively separate spacing elements may be disposed between adjacent stent segments, the spacing elements being movable with the stent segments along balloon member 70. Such spacing elements may be plastically deformable or self-expanding so as to be deployable with stent segments 32 into the vessel, but alternatively could be configured to remain on balloon member 70 following stent deployment; for example, such spacing elements could comprise elastic rings which elastically expand with balloon member 70 and resiliently return to their unexpanded shape when balloon member 70 is deflated. The spacing elements could be pushed to the distal end of balloon member 70 against stop 78 as additional stent segments 32 are advanced distally.

Stent segments 32 are preferably a malleable metal so as to be plastically deformable by expandable member 24 as they are expanded to the desired diameter in the vessel. Alternatively, stent segments 32 may be formed of an elastic or super elastic shape memory material such as Nitinol so as to self-expand upon release into the vessel by retraction of sheath 25. Stent segments 32 may also be composed of polymers or other suitable biocompatible materials. In self-expanding embodiments, expandable member 24 may also be used for predilatation of a lesion prior to stent deployment or for augmenting the expansion of the self-expanding stent segments.

In preferred embodiments, stent segments 32 are coated with a drug that inhibits restenosis, such as Rapamycin, Paclitaxel, analogs, prodrugs, or derivatives of the foregoing, or other suitable agent, preferably carried in a bioerodable polymeric carrier. Alternatively, stent segments 32 may be coated with other types of drugs and therapeutic materials such as antibiotics, thrombolytics, anti-thrombotics, anti-inflammatories, cytotoxic agents, anti-proliferative agents, vasodilators, gene therapy agents, radioactive agents, immunosuppressants, and chemotherapeutics. Such materials may be coated over all or a portion of the surface of stent segments 32, or stent segments 32 may include apertures, holes, channels, or other features in which such materials may be deposited.

Stent segments 32 may have a variety of configurations, including those described in copending application Ser. No. 60/440,839, filed Jan. 17, 2003, which is incorporated herein by reference. Other preferred stent configurations are described below. Stent segments 32 are preferably completely separate from one another without any interconnections, but alternatively may have couplings between two or more adjacent segments which permit flexion between the segments. As a further alternative, one or more adjacent stent segments may be connected by separable or frangible couplings that are separated prior to or upon deployment, as described in copending application Ser. No. 10/306,813, filed Nov. 27, 2002, which is incorporated herein by reference.

Figure 2B:
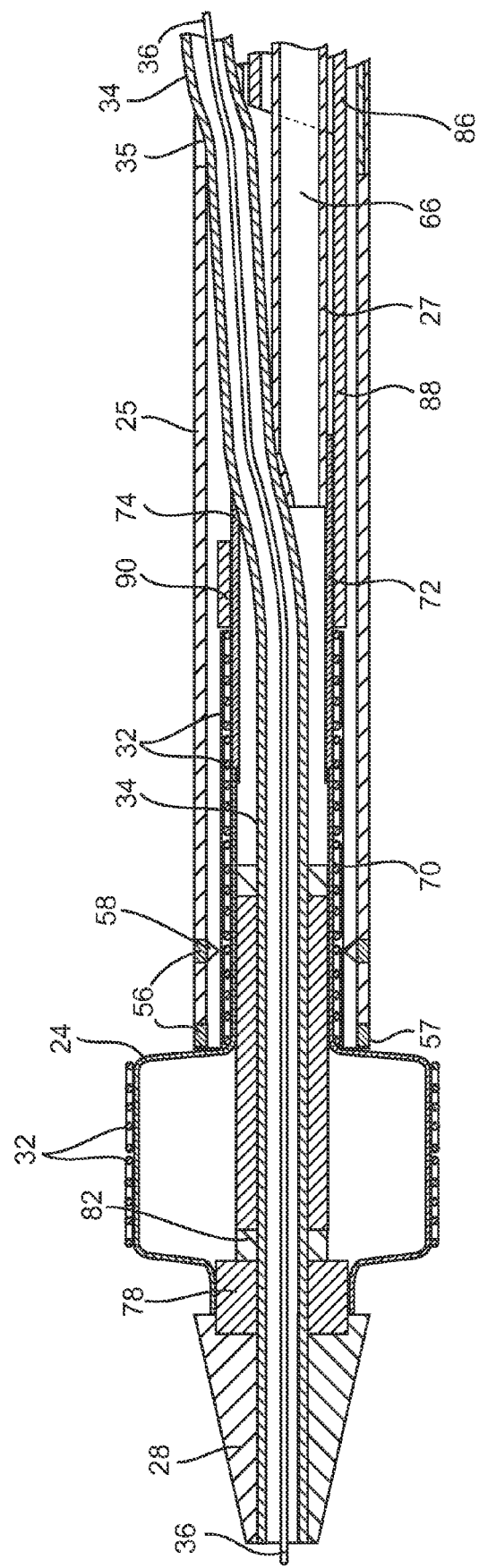
FIG. 2B is a side cross-section of a distal portion of the stent delivery catheter of FIG. 1 with expandable member inflated and sheath retracted.

A pusher tube 86 is slidably disposed over inner shaft 27 and has a distal extension 88 coupled to a pusher ring 90. Pusher ring 90 is slidable over tubular leg 72 and engages the stent segment 32 at the proximal end of the line of stent segments 32. At its proximal end (not shown), pusher tube 86 is coupled to sliding actuator 40 on handle 38 (see FIG. 1). In this way pusher tube 86 can be advanced distally relative to inner shaft 27 to urge stent segments 32 distally over expandable member 24 (or pusher tube 86 may be held in position while retracting expandable member 24 relative to stent segments 32) until the stent segments engage stop 78. In addition, pusher tube 86 can be used to hold stent segments 32 in place on expandable member 24 while sheath 25 is retracted to expose a desired number of stent segments 32, as shown in FIG. 2B. Pusher tube 86 may be constructed of a variety of biocompatible polymers or metals, preferably being stainless steel or Nitinol. Distal extension 88 and pusher ring 90 may be a polymer such as PTFE, FEP, polyimide, or Pebax, and are preferably reinforced with a metallic or polymeric braid to resist radial expansion when expandable member 24 is expanded.

It can be seen that with sheath 25 retracted a desired distance, expandable member 24 is allowed to expand when inflation fluid is delivered through inflation lumen 66, thereby expanding a desired number of stent segments 32 exposed distally of sheath 25. The remaining portion of expandable member 24 and the remaining stent segments 32 within sheath 25 are constrained from expansion by sheath 25.

FIG. 2B further illustrates that when sheath 25 is retracted relative to expandable member 24, guidewire tube exit port 35 becomes further away from the point at which guidewire 36 exits the proximal end 74 of tubular leg 72, increasing the distance that guidewire 36 must pass within the interior of sheath 25. Advantageously, guidewire tube 34 provides a smooth and continuous passage from the tubular leg 72 through guidewire tube exit port 35, eliminating any problems that might result from changing the alignment of the two. This is particularly important in the present invention where the stent delivery catheter may carry a large number of stent segments 32 and sheath 25 may be retracted a substantial distance relative to expandable member 24, resulting in substantial misalignment of guidewire tube exit port 35 relative to tubular leg 72.

In order to confirm the positioning of stent segments 32 on expandable member 24, fluoroscopy is used to visualize stent segments 32 relative to markers 82 on inner shaft 27. In addition, by fluoroscopic visualization of markers 56 on sheath 25 the user can see the extent of retraction of sheath 25 relative to expandable member 24 and view the location of the exposed stent segments 32 relative to sheath 25. Visualization of stent segments 32 is further enhanced with the use of radiopaque markers and/or materials in or on the stent segments themselves. Markers of radiopaque materials may be applied to the exterior of stent segments 32, e.g., by applying a metal such as gold, platinum, a radiopaque polymer, or other suitable coating or mark on all or a portion of the stent segments. Alternatively, stent segments 32 may include a radiopaque cladding or coating or may be composed of radiopaque materials such as L-605 cobalt chromium (ASTM F90), other suitable alloys containing radiopaque elements, or multilayered materials having radiopaque layers. In yet another alternative, stent segments 32 may have a geometry conducive to fluoroscopic visualization, such as having struts of greater thickness, sections of higher density, or overlapping struts. Some of the possible materials that may be used in stent segments 32 include (by ASTM number):

F67-00 Unalloyed Titanium

F75-01 Cobalt-28 Chromium-6 Molybdenum Alloy

F90-01 Wrought Cobalt-20 Chromium-15 Tungsten-10 Nickel Alloy

F136-02a Wrought Titanium-6 Aluminum-4 Vanadium ELI Alloy

Figure 5A:
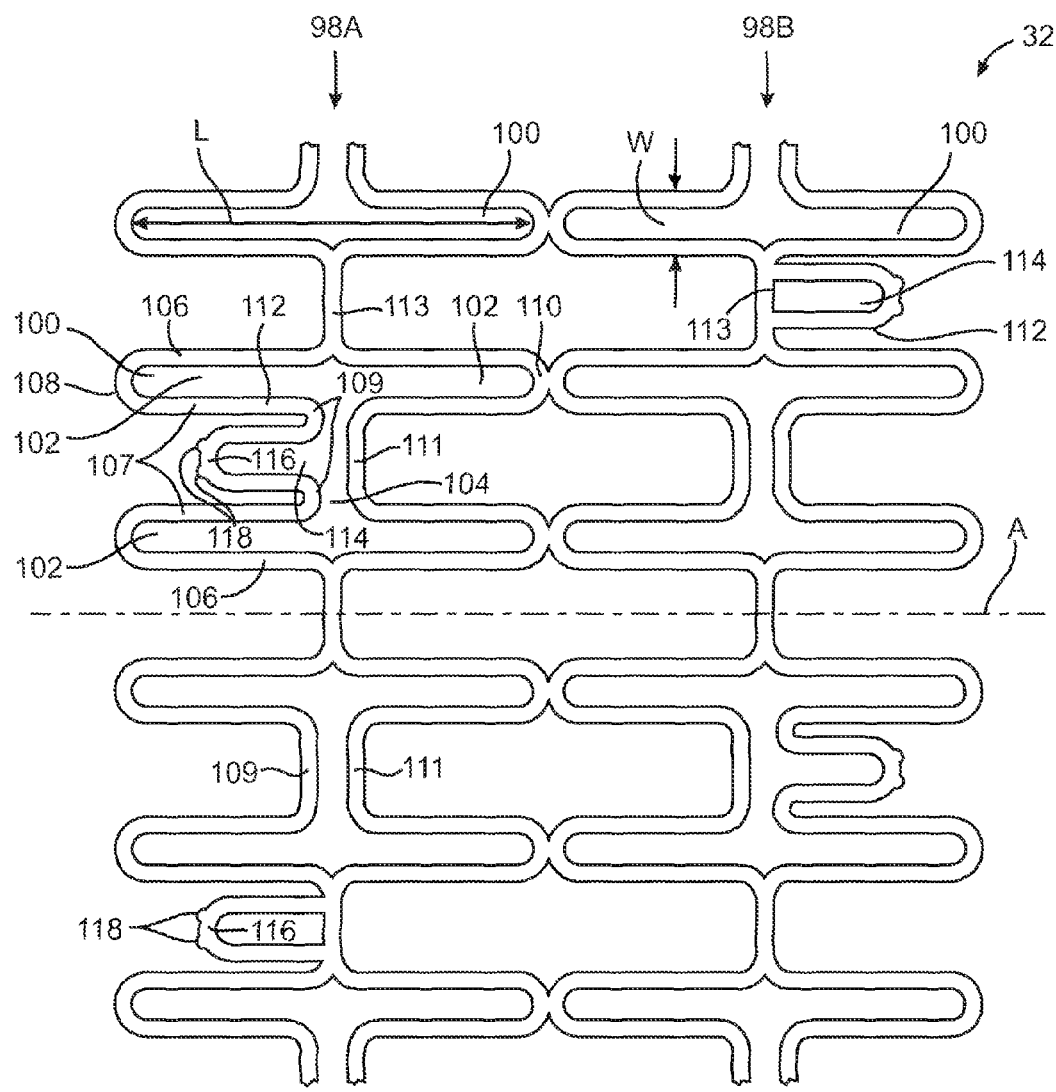
FIG. 5A is a side view of a first embodiment of a stent segment according to the invention in an unexpanded configuration.
Figure 5B:
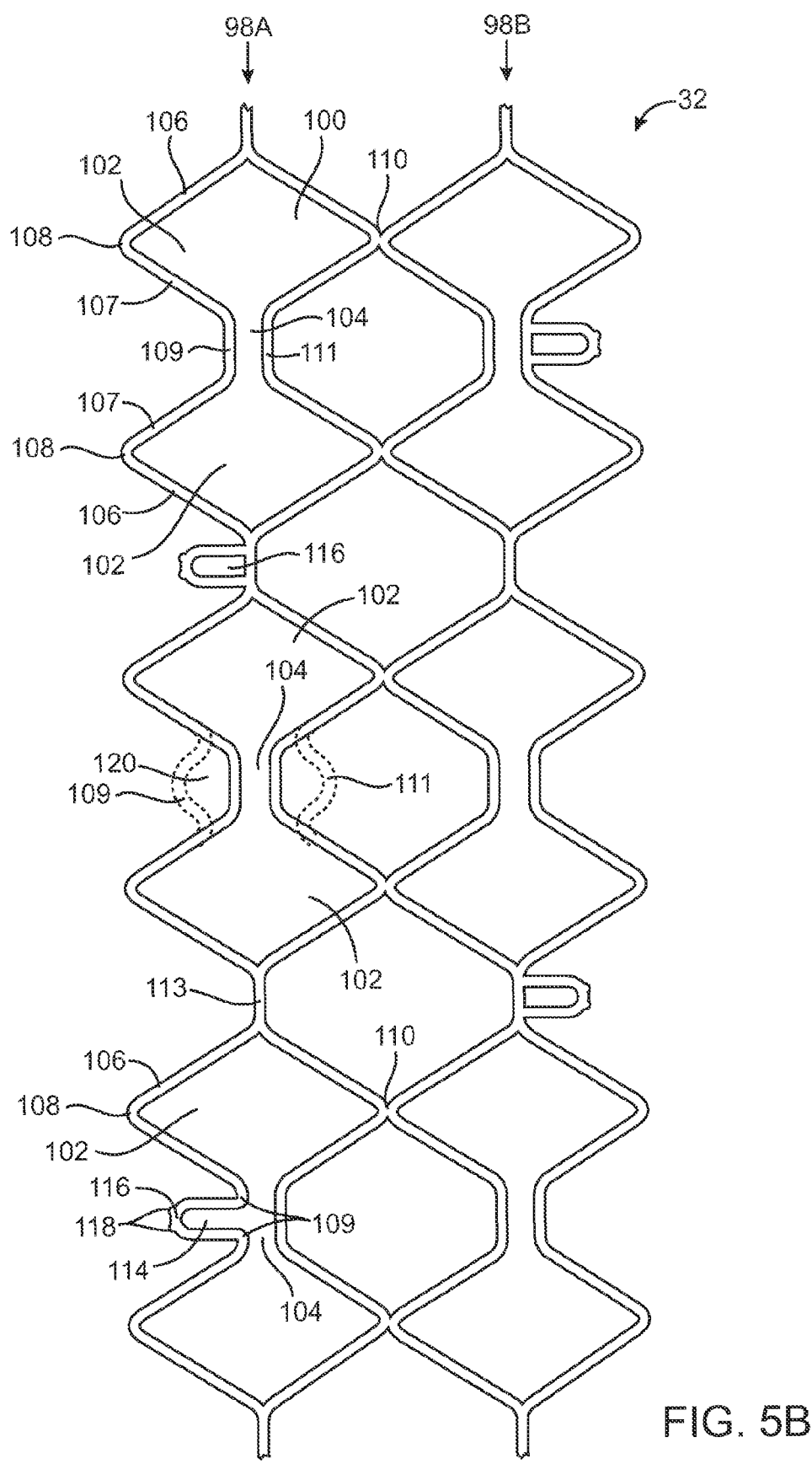
FIG. 5B is a side view of the stent segment of FIG. 5A in an expanded configuration.

F138-00, F139-00 Wrought 18 Chromium-14 Nickel-2.5 Molybdenum Stainless Steel Bar or Sheet F560-98 Unalloyed Tantalum F562-02 Wrought 35 Cobalt-35 Nickel-20 Chromium-10 Molybdenum Alloy F563-00 Wrought Cobalt-20 Nickel-20 Chromium 3.5 Molybdenum-3.5 Tungsten-5 Iron Alloy F688 Wrought Cobalt-35 Nickel-20 Chromium-10 Molybdenum Alloy F745-00 18 Chromium-12.5 Nickel-2.5 Molybdenum Stainless Steel F799-02 Cobalt-28 Chromium-6 Molybdenum Alloy F961-96 Cobalt-35 Nickel-20 Chromium-10 Molybdenum Alloy F1058-02 Wrought 40 Cobalt-20 Chromium-16 Iron-15 Nickel-7 Molybdenum Alloy F1091-02 Wrought Cobalt-20 Chromium-15 Tungsten-10 Nickel Alloy F1108 Titanium-6 Aluminum-4 Vanadium Alloy F1295-01 Wrought Titanium-6 Aluminum-7 Niobium Alloy F1314-01 Wrought Nitrogen-strengthened 22 Chromium-13 Nickel-5 Manganese-2.5 Molybdenum Stainless Steel Alloy F1241-99 Unalloyed Titanium Wire F1350-02 Wrought 18 Chromium-14 Nickel-2.5 Molybdenum Stainless Steel Wire F1377-98a Cobalt-28 Chromium-6 Molybdenum Powder coating F1472-02a Wrought Titanium-6 Aluminum-4 Vanadium Alloy F1537-00 Wrought Cobalt-28 Chromium-6 Molybdenum Alloy F1580-01 Titanium and Titanium-6 Aluminum-4 Vanadium Alloy Powder coating F1586-02 Wrought Nitrogen Strengthened 21 Chromium-10 Nickel-3 Manganese-2.5 Molybdenum Stainless Steel Bar F1713-96 Wrought Titanium-13 Niobium-13 Zirconium Alloy F1813-01 Wrought Titanium-12 Molybdenum-6 Zirconium-2 Iron Alloy F2063-00 Wrought Nickel-Titanium Shape Memory Alloys F2066-01 Wrought Titanium-15 Molybdenum Alloy F2146-01 Wrought Titanium-3 Aluminum-2.5 Vanadium Alloy Seamless Tubing F2181-02a Wrought Stainless Steel Tubing A first preferred geometry of stent segments 32 is illustrated in FIGS. 5A-5B. FIG. 5A illustrates a portion of a stent segment 32 in an unexpanded configuration, shown in a planar shape for clarity. Stent segment 32 comprises two parallel rows 98A, 98B of I-shaped cells 100 formed around an axis A so that stent segment 32 has a cylindrical shape. Each cell 100 has upper and lower axial slots 102 aligned with the axial direction and a circumferential slot 104. Upper and lower slots 102 preferably have an oval, racetrack, rectangular or other oblong shape with a long dimension L generally parallel to axis A and a short dimension W perpendicular thereto. Axial slots 102 are bounded by upper axial struts 106 and lower axial struts 107, curved outer ends 108 and curved inner ends 110. Each circumferential slot 104 is bounded by an outer circumferential strut 109 and an inner circumferential strut 111. Each I-shaped cell 100 is connected to the adjacent I-shaped cell 100 in the same row 98A or 98B by a circumferential connecting strut 113. All or a portion of cells 100 in row 98A merge or join with cells 100 in row 98B at the inner ends 110, which are integrally formed with the inner ends 110 of the adjacent cells 100.

In a preferred embodiment, a spacing member 112 extends outwardly in the axial direction from a selected number of outer circumferential struts 109 and/or connecting struts 113. Spacing member 112 preferably itself forms a subcell 114 in its interior, but alternatively may be solid without any cell or opening therein. For those spacing members 112 attached to outer circumferential struts 109, subcell 114 preferably communicates with I-shaped cell 100. Spacing members 112 are configured to engage the curved outer ends 108 of an adjacent stent segment 32 so as to maintain appropriate spacing between adjacent stent segments. In one embodiment, spacing members 112 have outer ends 116 with two spaced-apart protrusions 118 that provide a cradle-like structure to index and stabilize the curved outer end 108 of the adjacent stent segment. Preferably, spacing members 112 have an axial length of at least about 10%, more preferably at least about 25%, of the long dimension L of I-shaped cells 100, so that the I-shaped cells 100 of adjacent stent segments are spaced apart at least that distance. Because spacing members 112 experience little or no axial shortening during expansion of stent segments 32, this minimum spacing between stent segments is maintained both in the unexpanded and expanded configurations.

FIG. 5B shows stent segment 32 of FIG. 5A in an expanded configuration. It may be seen that cells 100 are expanded so that upper and lower slots 102 are diamond shaped with circumferential slots 104 remaining basically unchanged. This results in some axial shortening of the stent segment, thereby increasing the spacing between adjacent stent segments. The stent geometry is optimized by balancing the amount of axial shortening and associated inter-segment spacing, the desired degree of vessel wall coverage, the desired metal density, and other factors. Because the stent is comprised of multiple unconnected stent segments 32, any desired number from 2 up to 10 or more stent segments may be deployed simultaneously to treat lesions of any length. Further, because such segments are unconnected to each other, the deployed stent structure is highly flexible and capable of deployment in long lesions having curves and other complex shapes.

As an additional feature, circumferential slots 104 provide a pathway through which vessel side branches can be accessed for catheter interventions. Should stent segment 32 be deployed at a location in which it covers the ostium of a side branch to which access is desired, a balloon dilatation catheter may be positioned through circumferential slot 104 and expanded. This deforms circumferential struts 109, 111 axially outward, thereby expanding circumferential slot 104 and further expanding upper and lower slots 102, as shown in phantom in FIG. 3B. This provides a relatively large opening 120 through which a catheter may be inserted through stent segment 32 and into the side branch for placing stents, performing angioplasty, or carrying out other interventions.

Figure 6A:
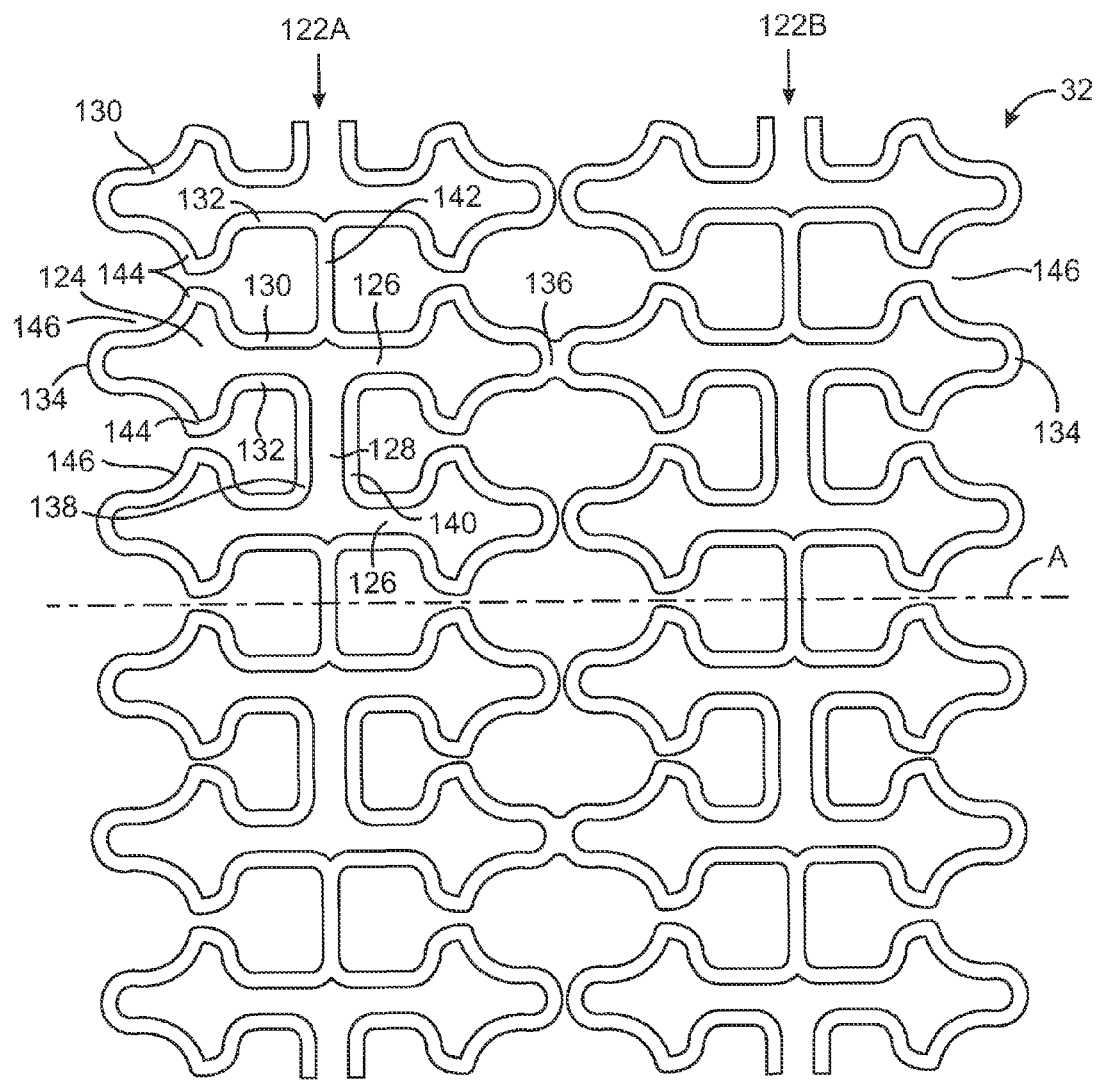
FIG. 6A is a side view of a second embodiment of a stent segment according to the invention in an unexpanded configuration.
Figure 6B:
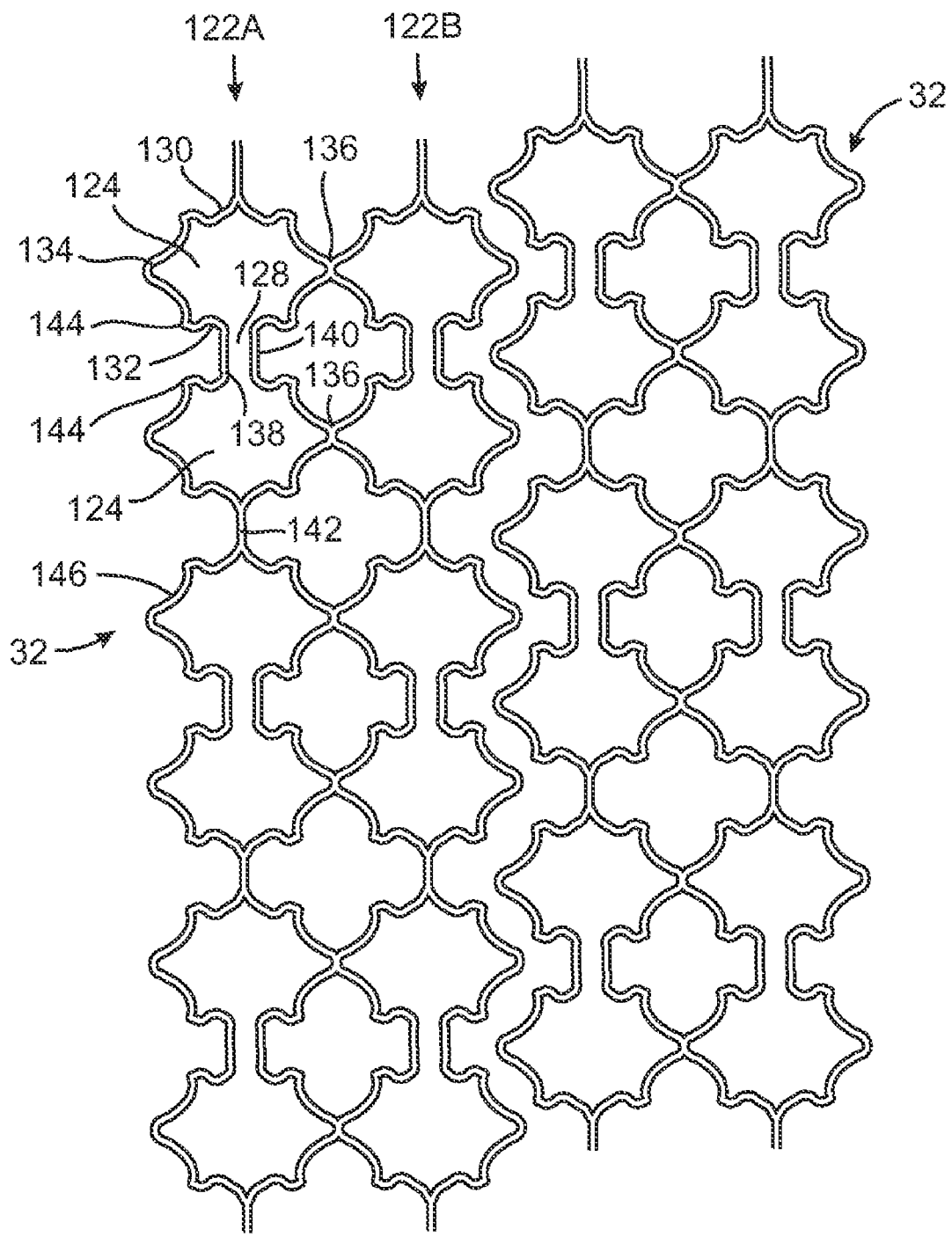
FIG. 6B is a side view of two of the stent segments of FIG. 6A in an expanded configuration.

FIGS. 6A-6B illustrate a second embodiment of a stent segment 32 according to the invention. In FIG. 6A, a portion of stent segment 32 is shown in a planar shape for clarity. Similar to the embodiment of FIG. 5A, stent segment 32 comprises two parallel rows 122A, 122B of I-shaped cells 124 formed into a cylindrical shape around axial axis A. Cells 124 have upper and lower axial slots 126 and a connecting circumferential slot 128. Upper and lower slots 126 are bounded by upper axial struts 130, lower axial struts 132, curved outer ends 134, and curved inner ends 136. Circumferential slots 128 are bounded by outer circumferential strut 138 and inner circumferential strut 140. Each I-shaped cell 124 is connected to the adjacent I-shaped cell 124 in the same row 122 by a circumferential connecting strut 142. Row 122A is connected to row 122B by the merger or joining of curved inner ends 136 of at least one of upper and lower slots 126 in each cell 124.

One of the differences between the embodiment of FIGS. 6A-6B and that of FIGS. 5A-5B is the way in which spacing is maintained between adjacent stent segments. In place of the spacing members 112 of the earlier embodiment, the embodiment of FIG. 6A includes a bulge 144 in upper and lower axial struts 130, 132 extending circumferentially outwardly from axial slots 126. These give axial slots 126 an arrowhead or cross shape at their inner and outer ends. The bulge 144 in each upper axial strut 130 extends toward the bulge 144 in a lower axial strut 132 in the same cell 100 or in an adjacent cell 100, thus creating a concave abutment 146 in the space between each axial slot 126. Concave abutments 146 are configured to receive and engage curved outer ends 134 of cells 124 in the adjacent stent segment, thereby maintaining spacing between the stent segments. The axial location of bulges 144 along upper and lower axial struts 130, 132 may be selected to provide the desired degree of inter-segment spacing.

FIG. 6B shows two stent segments 32 of FIG. 6A in an expanded condition. It may be seen that axial slots 124 are deformed into a circumferentially widened modified diamond shape with bulges 144 on the now diagonal upper and lower axial struts 130, 132. Circumferential slots 128 are generally the same size and shape as in the unexpanded configuration. Bulges 144 have been pulled away from each other to some extent, but still provide a concave abutment 146 to maintain a minimum degree of spacing between adjacent stent segments. As in the earlier embodiment, some axial shortening of each segment occurs upon expansion and stent geometry can be optimized to provide the ideal intersegment spacing.

It should also be noted that the embodiment of FIGS. 6A-6B retains the feature described above with respect to FIGS. 5A-5B to enable access to vessel side branches blocked by stent segment 32. Should such side branch access be desired, a dilatation catheter may be inserted into circumferential slot 128 and expanded to provide an enlarged opening through which a side branch may be entered.

Referring now to FIGS. 7A-7E, the use of the stent delivery catheter of the invention will be described. While the invention will be described in the context of coronary artery treatment, the invention is useful in any of a variety of blood vessels and other body lumens in which stents are deployed, including the carotid, femoral, iliac and other arteries, as well as veins and other fluid-carrying vessels. A guiding catheter (not shown) is first inserted into a peripheral artery such as the femoral and advanced to the ostium of the target coronary artery. A guidewire GW is then inserted through the guiding catheter into the coronary artery A where lesion L is to be treated. The proximal end of guidewire GW is then inserted through nosecone 28 and guidewire tube 34 outside the patient's body and stent delivery catheter 20 is slidably advanced over guidewire GW and through the guiding catheter into the coronary artery A. Stent delivery catheter 20 is positioned through a lesion L to be treated such that nosecone 28 is distal to lesion L. During this positioning, sheath 25 is positioned distally up to nosecone 28 so as to surround expandable member 24 and all of the stent segments 32 thereon.

Optionally, lesion L may be predilated prior to stent deployment. Predilatation may be performed prior to introduction of stent delivery catheter 20 by inserting an angioplasty catheter over guidewire GW and dilating lesion L. Alternatively, stent delivery catheter 20 may be used for predilitation by retracting sheath 25 along with stent segments 32 to expose an extremity of expandable member 24 long enough to extend through the entire lesion. This may be done while delivery catheter 20 is positioned proximally of lesion L or with expandable member 24 extending through lesion L. Fluoroscopy enables the user to visualize the extent of sheath retraction relative to lesion L by observing the position of marker 56 on sheath 25 relative to marker 82 at the distal end of expandable member 24. To allow stent segments 32 to move proximally relative to expandable member 24, force is released from pusher tube 86 and valve member 58 engages and draws the stent segments proximally with sheath 25. With the appropriate length of expandable member 24 exposed, expandable member 24 is positioned within lesion L and inflation fluid is introduced through inflation lumen 66 to inflate expandable member 24 distally of sheath 25 and thereby dilate lesion L. Expandable member 24 is then deflated and retracted within sheath 25 while maintaining force on pusher tube 86 so that stent segments 32 are positioned up to the distal end of expandable member 24, surrounded by sheath 25. Alternative embodiments of devices and methods for lesion predilatation are described in detail below.

Figure 7A:
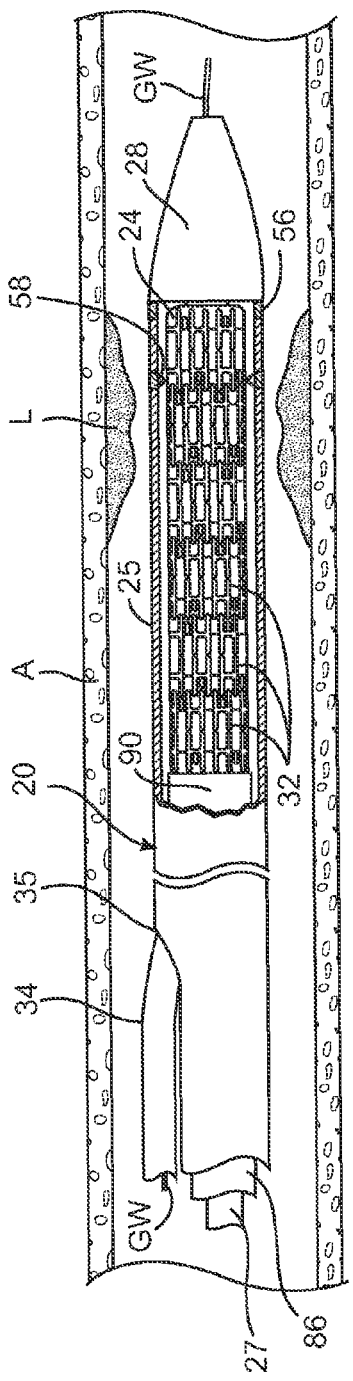
Figure 7B:
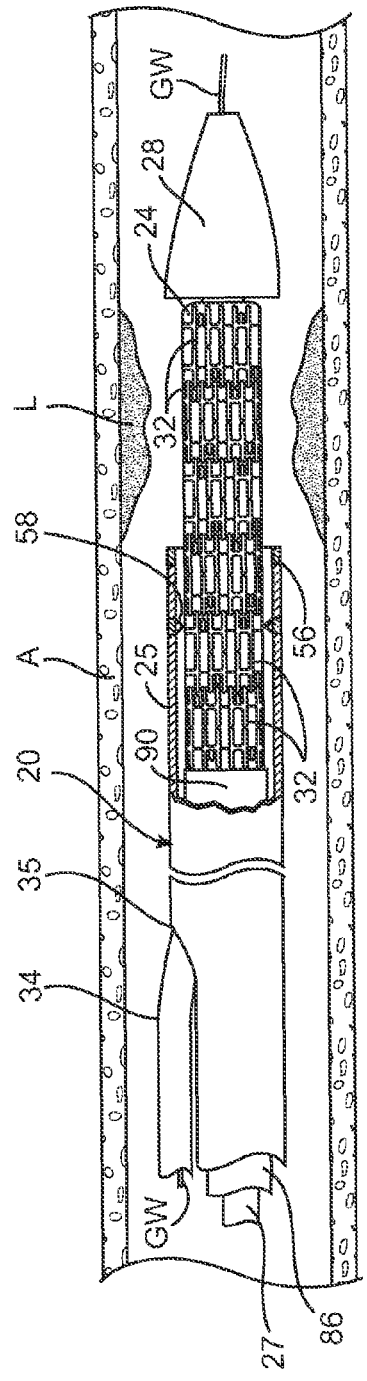

Following any predilatation, stent delivery catheter 20 is repositioned in artery A so that nosecone 28 is distal to lesion L as shown in FIG. 7A. Sheath 25 is then retracted as in FIG. 7B to expose the appropriate number of stent segments 32 to cover lesion L. Again, fluoroscopy can be used to visualize the position of sheath 25 by observing marker 56 thereon relative to marker 82 within expandable member 24. As sheath 25 is drawn proximally, force is maintained against pusher tube 86 so that stent segments 32 remain positioned up to the distal end of expandable member 24. It should also be noted that sheath 25 moves proximally relative to guidewire tube 34, which slides through guidewire tube exit port 35. Advantageously, regardless of the position of sheath 25, guidewire tube 34 provides a smooth and continuous passage for guidewire GW so that stent delivery catheter slides easily over guidewire GW.

Figure 7C:
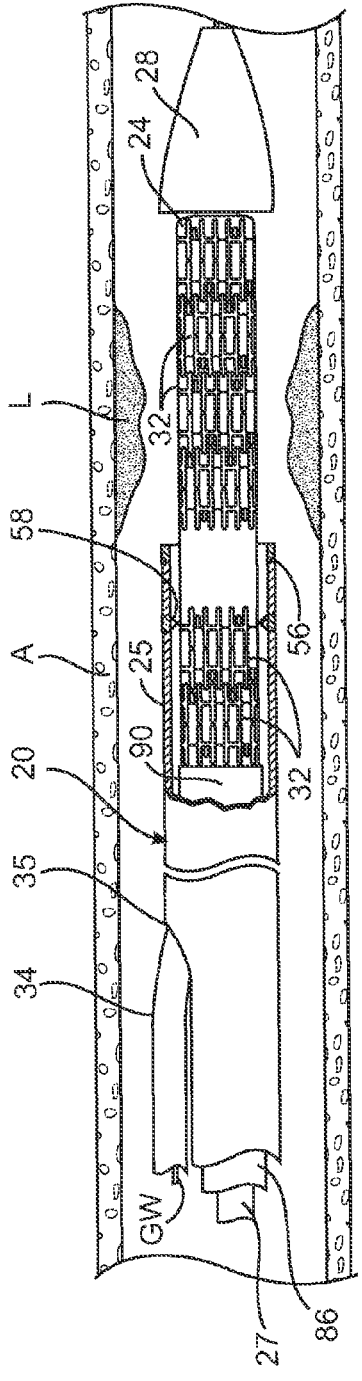

With the desired number of stent segments 32 exposed distally of sheath 25, it is frequently desirable to create some spacing between the stent segments to be deployed and those remaining enclosed within sheath 25. This reduces the risk of dislodging or partially expanding the distal-most stent segment 32 within sheath 25 when expandable member 24 is inflated. Such spacing is created, as shown in FIG. 7C, by releasing force against pusher tube 86 and retracting sheath 25 further proximally a short distance. The engagement of valve member 58 with stent segments 32 moves those stent segments 32 within sheath 25 away from those stent segments 32 distal to sheath 25. The length of this spacing is preferably equal to the length of about ½-1 stent segment.

Expandable member 24 is then inflated by delivering inflation fluid through inflation lumen 66, as shown in FIG. 7D. The exposed distal portion of expandable member 24 expands so as to expand stent segments 32 thereon into engagement with lesion L. If predilatation was not performed, lesion L may be dilated during the deployment of stent segments 32 by appropriate expansion of expandable member 24. Sheath 25 constrains the expansion of the proximal portion of expandable member 24 and those stent segments 32 within sheath 25.

Figure 8:
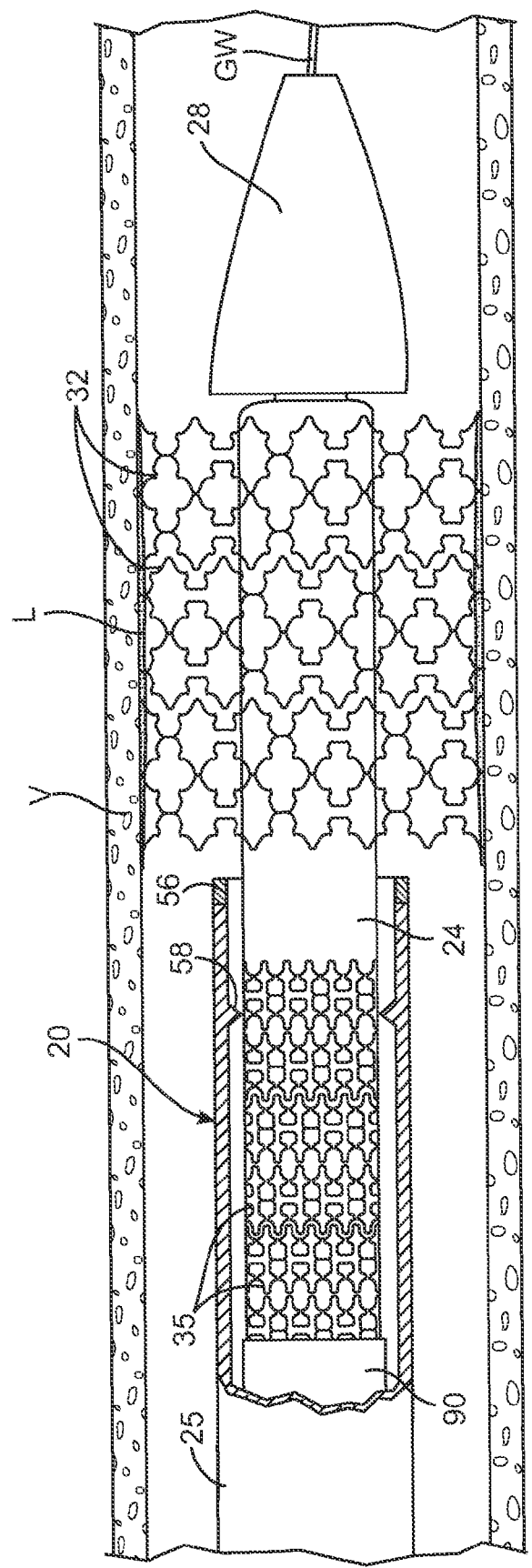
FIG. 8 is a side cut-away view of the stent delivery catheter of the invention positioned in a vessel with the stent segments of FIGS. 6A-6B in a deployed configuration.

Expandable member 24 is then deflated, leaving stent segments 32 in a plastically-deformed, expanded configuration within lesion L, as shown in FIG. 7E. The alternative embodiment of stent segment 32 illustrated in FIGS. 6A-6B is shown in a similarly expanded condition in FIG. 8. With stent segments 32 deployed, expandable member 24 may be retracted within sheath 25, again maintaining force against pusher tube 86 to position stent segments 32 at the distal end of expandable member 24. Expandable member 24 is moved proximally relative to stent segments 32 until the distal-most stent segment engages stop 78 (FIGS. 2A-2B), thereby placing stent segments 32 in position for deployment. Stent delivery catheter 20 is then ready to be repositioned at a different lesion in the same or different artery, and additional stent segments may be deployed. During such repositioning, guidewire tube 34 facilitates smooth tracking over guidewire GW. Advantageously, multiple lesions of various lengths may be treated in this way without removing stent delivery catheter 20 from the patient's body. Should there be a need to exchange stent delivery catheter 20 with other catheters to be introduced over guidewire GW, guidewire tube 34 facilitates quick and easy exchanges.

When the movement of the pusher tube, sheath, or stent segments is described in relation to other components of the delivery catheter of the invention, such movement is relative and will encompass both moving the sheath, pusher tube, or stent segments while keeping the other component(s) stationary, keeping the sheath, pusher tube or stent segments stationary while moving the other component(s), or moving multiple components simultaneously relative to each other.

While the foregoing description of the invention is directed to a stent delivery catheter for deploying stents into vascular lumens to maintain patency, various other types of wire-guided catheters also may embody the principles of the invention. For example, balloon catheters for angioplasty and other purposes, particularly those having a slidable external sheath surrounding the balloon, may be constructed in accordance with the invention. Other types of catheters for deployment of prosthetic devices such as embolic coils, stent grafts, aneurism repair devices, annuloplasty rings, heart valves, anastomosis devices, staples or clips, as well as ultrasound and angiography catheters, electrophysiological mapping and ablation catheters, and other devices may also utilize the principles of the invention.

Although the above is complete description of the preferred embodiments of the invention, various alternatives, additions, modifications and improvements may be made without departing from the scope thereof, which is defined by the claims.

What is claimed is:

1. A method of treating a lesion in a body lumen between a distal treatment boundary and a proximal treatment boundary, the method comprising:
   positioning a catheter in the body lumen, the catheter having a catheter body with a longitudinal axis which carries a prosthesis positionable over an expandable member and a sheath positionable over the prosthesis, wherein the prosthesis comprises a plurality of separable prosthetic segments, and wherein the sheath comprises an inwardly extending valve member disposed on an inside surface of a distal portion of the sheath and a distal extremity reinforced so as to resist radial expansion when the expandable member is expanded;
   moving the catheter though the body lumen until a distal end of the prosthesis is disposed at or distal to the distal treatment boundary;
   maintaining the position of the catheter body in the body lumen while retracting the sheath relative to the catheter body and fluoroscopically viewing a radiopaque sheath marker on the sheath until the radiopaque sheath marker is disposed within a predetermined distance of the proximal treatment boundary, wherein a deployable portion of the prosthesis, the deployable portion comprising a first plurality of the prosthetic segments, is exposed outside the sheath in an unexpanded condition and a retained portion of the prosthesis remains covered by the sheath and wherein a proximal end of the deployable portion is disposed at or proximal to the proximal treatment boundary;
   axially separating the unexpanded deployable portion from the retained portion of the prosthesis to create a space between the deployable portion and the retained portion along the longitudinal axis of the catheter body by engaging the retained portion of the prosthesis with the valve member and moving the retained portion away from the unexpanded deployable portion; and
   radially expanding the entire deployable portion of the prosthesis as a single portion while the retained portion remains covered by the sheath, wherein the expanded deployable portion extends from the proximal treatment boundary to the distal treatment boundary.

2. The method of claim 1, wherein the step of moving the catheter comprises fluoroscopically viewing a radiopaque distal marker on the catheter body, the catheter being moved until the radiopaque distal marker is disposed within a predetermined distance from the distal treatment boundary.

3. The method of claim 1, wherein the radiopaque sheath marker is at a distal end of the sheath, and the sheath is retracted until the radiopaque sheath marker is proximal to the proximal treatment boundary.

4. The method of claim 3, wherein the radiopaque sheath marker comprises a marker band affixed to the sheath.

5. The method of claim 1, wherein the prosthetic segments are axially movable over the expandable member.

6. The method of claim 5, further comprising axially moving a prosthetic segment of the retained portion distally on the expandable member after expanding the first plurality.

7. The method of claim 5, wherein the prosthetic segments are positionable at a predetermined position on the expandable member relative to the radiopaque distal marker.

8. The method of claim 1, further comprising constraining a proximal portion of the expandable member with the reinforced distal extremity of the sheath as the deployable portion is radially expanded with a distal portion of the expandable member.

9. The method of claim 1, wherein separating comprises axially separating a proximal prosthetic segment in the deployable portion from a second prosthetic segment in the retained portion.

10. The method of claim 9, wherein moving the retained portion away comprises engaging the second prosthetic segment with the valve member on the sheath, and further retracting the sheath relative to the catheter body.

11. The method of claim 10, wherein the sheath is further retracted while fluoroscopically viewing a radiopaque sheath marker thereon relative to the proximal prosthetic segment until a desired separation distance is disposed therebetween.

12. The method of claim 9, wherein the deployable portion is expanded by an expandable member positioned within the prosthetic segments, the proximal prosthetic segment being axially separated so as to allow the expandable member to fully expand the prosthetic segments in the deployable portion without expanding any portion of the second prosthetic segment.

13. The method of claim 12, wherein upon expansion the expandable member has a tapered region which tapers from an expanded diameter outside the sheath to a constrained diameter inside the sheath, the proximal prosthesis being axially separated such that no prosthetic segments are disposed over the tapered region.

14. The method of claim 1, further comprising without removing the catheter from the body lumen:
   returning the sheath to a distal position on the catheter body;
   repositioning the catheter to a second treatment site in the body lumen;
   retracting the sheath to expose a third portion of the prosthesis outside the sheath; and
   radially expanding the third portion of the prosthesis in the body lumen.

15. A method of treating a lesion in a body lumen between a distal treatment boundary and a proximal treatment boundary, the method comprising:
- positioning a catheter in the body lumen, the catheter having a catheter body with a longitudinal axis, an expandable member coupled to the catheter body, a plurality of separable tubular prostheses positionable over the expandable member, and a sheath positionable over the prostheses, wherein the sheath comprises an inwardly extending valve member disposed on an inside surface of a distal portion of the sheath and a distal extremity reinforced so as to resist radial expansion when the expandable member is expanded;
- moving the catheter in the body lumen until a distal prosthesis is positioned at or distal to the distal treatment boundary;
- maintaining the position of the catheter body in the body lumen while retracting the sheath relative to the catheter body until a first plurality of the prostheses are exposed outside the sheath in an unexpanded configuration, wherein at least a second prosthesis remains covered by the sheath and wherein a proximal prosthesis in the first plurality is positioned at or proximal to the proximal treatment boundary;
- axially separating the unexpanded first plurality of the prostheses from the second prosthesis covered by the sheath to create a space between the first plurality of prostheses and the second prosthesis along the longitudinal axis of the catheter body by engaging the second prosthesis with the valve member and moving the second prosthesis away from the unexpanded first plurality of prostheses; and
- expanding the expandable member to radially expand all of the first plurality of prostheses at the same time so that the first plurality of prostheses extend from the distal treatment boundary to the proximal treatment boundary after expansion.

16. The method of claim 15, wherein the step of moving the catheter through the body lumen comprises fluoroscopically viewing a radiopaque distal marker on the catheter body, the catheter being moved until the radiopaque distal marker is disposed within a predetermined spacing from the distal treatment boundary.

17. The method of claim 16, wherein the plurality of prostheses are positionable at a predetermined position on the expandable member relative to the radiopaque distal marker.

18. The method of claim 15, wherein the sheath is retracted while fluoroscopically viewing a radiopaque sheath marker thereon until the radiopaque sheath marker is disposed within a second predetermined distance from the proximal treatment boundary.

19. The method of claim 18, wherein the radiopaque sheath marker is disposed at the distal end of the sheath.

20. The method of claim 15, wherein the plurality of prostheses are axially movable over the expandable member.

21. The method of claim 20, further comprising axially moving the second prosthesis distally on the expandable member after expanding the first plurality.

22. The method of claim 15, further comprising constraining a proximal portion of the expandable member with the reinforced distal extremity of the sheath as the first plurality is radially expanded with a distal portion of the expandable member.

23. The method of claim 15, wherein the first plurality of prostheses comprises a plurality of prosthetic segments unconnected to each other prior to expansion.

24. The method of claim 15, wherein axially separating comprises engaging the second prosthesis with the valve member on the sheath, and further retracting the sheath relative to the catheter body.

25. The method of claim 24, wherein the sheath is further retracted while fluoroscopically viewing the radiopaque sheath marker relative to the proximal prosthesis until a desired separation distance is disposed therebetween.

26. The method of claim 15, wherein the first plurality of prostheses are axially separated from the second prosthesis to allow the expandable member to fully expand all of the first plurality of prostheses without expanding any portion of the second prosthesis.

27. The method of claim 15, wherein upon expansion the expandable member has a tapered region which tapers from an expanded diameter outside the sheath to a constrained diameter inside the sheath, the first plurality of prostheses being axially separated from the sheath such that none of the prostheses are disposed over the tapered region.

28. The method of claim 15, further comprising without removing the catheter from the body lumen:
- returning the sheath to a distal position on the catheter body;
- repositioning the catheter to a second treatment site in the body lumen;
- retracting the sheath to expose a third plurality of prostheses outside the sheath; and
- expanding the expandable member to radially expand the third plurality of prostheses in the body lumen.

29. A method of deploying a prosthesis in a vascular lesion having proximal and distal boundaries, comprising:
- positioning a catheter across the vascular lesion such that a distal end of the catheter is distal to the distal boundary, the catheter carrying the prosthesis positionable over an expandable member, wherein the prosthesis comprises a plurality of separable prosthetic segments covered by a sheath, and wherein the sheath comprises an inwardly extending valve member disposed on an inside surface of a distal portion of the sheath and a distal extremity reinforced so as to resist radial expansion when the expandable member is expanded;
- maintaining the position of the catheter in the body lumen while retracting the sheath under fluoroscopic visualization until a distal end of the sheath is visualized as being proximal to the proximal boundary, wherein a deployable portion of the prosthesis is exposed outside the sheath in an unexpanded condition while a retained portion of the prosthesis remains covered by the sheath, wherein the deployable portion comprises a first plurality of prosthetic segments and the retained portion comprises one or more prosthetic segments;
- axially separating the unexpanded first plurality of the prostheses from the retained portion to create a space between the first plurality and the retained portion along the longitudinal axis of the catheter body, wherein separating comprises engaging the retained portion with the valve member and moving the retained portion away from the unexpanded first plurality; and
- radially expanding the entire deployable portion as a single portion with the expandable member while the retained portion of the prosthesis remains covered by the sheath, wherein the expanded deployable portion extends between the proximal and distal boundaries.

30. The method of claim 29, wherein the step of positioning the catheter comprises fluoroscopically viewing a radiopaque distal marker on the catheter body, the catheter being moved until the radiopaque distal marker is disposed within a predetermined distance from the distal boundary.

31. The method of claim 29, wherein the sheath has a radiopaque sheath marker on the distal end thereof, and the sheath is retracted until the radiopaque sheath marker is proximal to the proximal boundary.

32. The method of claim 29, wherein the prostheses are axially movable over the expandable member.

33. The method of claim 32, further comprising axially moving the retained portion distally on the expandable member after expanding the first plurality.

34. The method of claim 32, wherein the plurality of prosthetic segments are positionable at a predetermined position on the expandable member relative to the radiopaque distal marker.

35. The method of claim 29, further comprising constraining a proximal portion of the expandable member with the reinforced distal extremity sheath as the deployable portion is radially expanded with a distal portion of the expandable member.

36. The method of claim 29, wherein axially separating comprises engaging the retained portion with the valve member on the sheath, and further retracting the sheath relative to the catheter body.

37. The method of claim 36, wherein the sheath is further retracted while fluoroscopically viewing a radiopaque sheath marker thereon relative to the proximal prosthetic segment until a desired separation distance is disposed therebetween.

38. The method of claim 29, wherein the deployable portion is expanded by an expandable member positioned within the prosthetic segments, the first plurality being axially separated so as to allow the expandable member to fully expand each of the prosthetic segments in the deployable portion without expanding any portion of the retained portion.

39. The method of claim 38, wherein upon expansion the expandable member has a tapered region which tapers from an expanded diameter outside the sheath to a constrained diameter inside the sheath, the deployable portion being axially separated such that no prosthetic segments are disposed over the tapered region.

40. The method of claim 29, further comprising without removing the catheter from the body lumen:
  returning the sheath to a distal position on the catheter body;
  repositioning the catheter to a second treatment site in the body lumen;
  retracting the sheath to expose a third portion of the prosthesis outside the sheath; and
  radially expanding the third portion of the prosthesis in the body lumen.

* * * * *